US007358053B2

(12) United States Patent
Prichard et al.

(10) Patent No.: US 7,358,053 B2
(45) Date of Patent: Apr. 15, 2008

(54) METHODS FOR DETECTING AND REVERSING RESISTANCE TO MACROCYCLIC LACTONE COMPOUNDS

(75) Inventors: Roger K. Prichard, Beaconsfield (CA); Ming Xu, Chino, CA (US); Ana Paula Ribeiro, Montreal (CA); William J. Blackhall, Pointe Claire (CA); Robin N. Beech, Beaconsfield (CA); Marcelo Molento, Sainte-Anne-de-Bellevue (CA); Hao Yuan Liu, Newton, MA (US)

(73) Assignee: McGill Univeristy, Montreal, Quebec (CA)

( * ) Notice: Subject to any disclaimer, the term of this patent is extended or adjusted under 35 U.S.C. 154(b) by 323 days.

(21) Appl. No.: 10/456,815

(22) Filed: Jun. 6, 2003

(65) Prior Publication Data

US 2003/0190666 A1    Oct. 9, 2003

Related U.S. Application Data

(62) Division of application No. 09/749,340, filed on Dec. 27, 2000, now Pat. No. 6,593,087, which is a division of application No. 09/067,676, filed on Apr. 28, 1998, now Pat. No. 6,403,308.

(60) Provisional application No. 60/045,160, filed on Apr. 30, 1997.

(51) Int. Cl.
G01N 33/53    (2006.01)
(52) U.S. Cl. ..................................... 435/7.1; 436/547
(58) Field of Classification Search ................... 435/7.1
See application file for complete search history.

(56) References Cited

U.S. PATENT DOCUMENTS

| | | | |
|---|---|---|---|
| 3,950,360 A | 4/1976 | Aoki et al. ................. 549/264 |
| 4,199,569 A | 4/1980 | Chabala et al. ............... 514/30 |
| 4,310,519 A | 1/1982 | Albers-Schonberg et al. . 514/30 |
| 4,837,306 A * | 6/1989 | Ling et al. ............... 530/388.2 |
| 4,916,154 A | 4/1990 | Asato et al. ................ 514/450 |
| 5,106,994 A | 4/1992 | Carter et al. ............... 549/264 |
| 5,169,956 A | 12/1992 | Carter et al. ............... 549/264 |
| 5,238,936 A | 8/1993 | Regnier et al. |
| 5,332,577 A | 7/1994 | Gertner et al. .............. 424/443 |
| 5,583,008 A | 12/1996 | Johnson et al. ............... 435/29 |
| 5,648,085 A * | 7/1997 | Lanning et al. ............. 424/405 |
| 5,733,566 A | 3/1998 | Lewis ........................ 424/422 |

FOREIGN PATENT DOCUMENTS

| | | |
|---|---|---|
| EP | 0502788 A1 | 9/1992 |
| WO | 95/09246 | 4/1995 |

OTHER PUBLICATIONS

Lanning et al. Biochimica et Biophysica Acta, 1291:155-162, 1996.*
Lodish et al., Mol. Cell Biol., 3rd ed. Scientific American Books, NY, 1995, p. 115.*
Haynes et al. (Electrophoresis, 19:1862-1871, 1998.*
Bork (Genome Res., 10:398-400, 2000.*
Xu et al., The Molecular Basis of Ivermectin Resistance in *Haemonchus contortus*, oral presentation at 41st Annual Meeting, Jul. 20-23, 1996 (KY) AAVP Proceedings abstr. 100.
Ford, Modulators of Multidrug Resistance, Hematol. Oncol. Clinics North America 9(2):337-361 (Apr. 1995).
Lincke et al., The expression of two P-glycoprotein (*pgp*) genes in transgenic *Caenorhabditis elegans* is confined to intestinal cells, EMBO J. 12(4):1615-1620 (1993).
Lincke et al., The P-glycoprotein Gene Family of *Caenorhabditis elegans* Cloning & Characterization of Genomic & Complementary DNA Sequences, J. Mol. Biol. 228:701-711 (1992).
Schinkel et al., Disruption of the Mouse *mdr 1a* P-Glycoprotein Gene Leads to a Deficiency in the Blood-Brain Barrier and to Increased Sensitivity to Drugs, Cell 77:491-502 (May 20, 1994).
Sangster, P-glycoproteins in Nematodes, Parasitology Today 10(8):319-322 (1994).
Sangster et al., A P-Glycoprotein Gene Family From *Haemonchus contortus*, J. Cell Biochem. 17(Supp.): 119 (1993), abstr. 1223.
Lee et al., Generation of cDNA Probes Directed by Amino Acid Sequence: Cloning of Urate Oxidase, Science 239:1288-1291 (Mar. 1988).
Sarkadi et al., Expression of the Human Multidrug Resistance cDNA in Insect Cells Generates a High Activity Drug-simulated Membrane ATPase, J. Biol. Chem. 267(7):4854-4858 (Mar. 1992).
Broeks et al., A P-glycoprotein protects *Caenorhabditis elegans* against natural toxins, EMBO J., 14(9):1858-1866 (1995).
Xu et al., Ivermectin resistance in nematodes may be caused by alteration of P-glycoprotein homolog, Mol. & Biochem. Parasitol. 91(2):327-335 (Mar. 15, 1998).

(Continued)

*Primary Examiner*—Robert A. Zeman
*Assistant Examiner*—Brian J Gangle
(74) *Attorney, Agent, or Firm*—Barbara L. Renda; Anne M. Rosenblum

(57) ABSTRACT

This invention describes novel purified and isolated nucleic acid molecules or the fragments thereof, extracted from nematode or arthropod pests or recombinant, which encode P-glycoprotein homologs and regulate resistance to the macrocyclic lactone compounds. The invention further relates to the new P-glycoprotein homolog expression product of these nucleic acids. Also described herein are methods for detecting the gene encoding for resistance to the macrocyclic lactone compounds in nematode or arthropod pests which comprise comparing the nucleic acids extracted from a pest specimen to the nucleic acids encoding for resistance and the nucleic acids encoding for susceptibility to the macrocyclic lactone compounds. Lastly, the present invention is also drawn to methods and compositions for increasing the efficacy of the macrocyclic lactone compounds against resistant nematode or resistant arthropod pests which comprise administering to a mammal or applying to crops and the like a pesticidal enhancing effective amount of a multidrug resistance reversing agent.

3 Claims, 24 Drawing Sheets

OTHER PUBLICATIONS

Kwa et al., Use of P-glycoprotein gene probes to investigate anthelmintic resistance in *Haemonchus contortus* and comparison with *Onchocerca volvulus*, Internat. J. Parasitol. 28:1235-1240 (Aug. 1998).

Nare et al., p-Azidosalicyl-5-amino-6-phenoxybenzimidazole Photolabels the N-terminal 63-103 Amino Acids of *Haemonchus contortus* β-Tubulin 1, J. Biol. Chem. 271:8575-8581 (1996).

* cited by examiner

```
  1 ACGGTGGCGT TTGTTGGGCA GTCTGGTTGT GGAAAAAGCA CTGTGAAGGC GTTGTTGGAA
 61 CGGTTTTACA ATCAAAACAA GGGCGTGATT ACGGACGCCG AAACATCAG
121 ATACGCAATC TTCGTGAGCA AGTGTGTATT GTAAGCCAGG AACCAACGCT GTTCGACTGT
181 ACCATCATGG AAAACATCTG TTACGTCTC GATGACCCCA AGCTCCTACG AACAGGTTGT
241 TGCTGCAGCA AAATCGGTCG AGTGAAATG GCGAACATTC ACAATTTTGT GCTGGGACTA
301 CCAGAGGGTT ACGATACGCG TGTTGGTGAG AAAGGCACTC AGCTGTCAGG CGGACAGAAG
361 AAACGAATAG CCATAGCCAG AGCGCTGATT CGAGATCCGC CTATACTTCT GCTGGATGAG
421 GCTACGACGG CC
```

FIG. 2A

```
  1 TVAFVGQSGC GKSTVKALLE RFYNQNKGVI TDAENIRMN IRNLREQVCI VSQEPTLFDC
 61 TIMENICYGL DDPKLLRTGC CCSKIGRVEM ANIHNFVLGL PEGYDTRVGE KGTQLSGGQK
121 KRIAIARALI RDPPILLLDE ATTA
```

FIG. 2B

```
   1 GGTTTAATTA CCCAAGTTTG AGAGATCGTT CTCAAGCTGG TAAAATGTTC GAAAAAGGCC
  61 AAGATGATGA ACGTATACCA TTACTCGGTT CATCCAAGAA AAGTTCAATC GGCGAAGTCA
 121 GTAAAAAAGA AGAACCGCCT ACAATAACAA ACCGTGGAAT TCTCTCCTTA GCCACTACAT
 181 TGGATTATGT GCTTCTTGCG GCTGGTACGC TGGCGCCGTG TGTTCATGGC GCTGGATTCT
 241 CAGTACTCGG TATTGTACTC GGTGGTATGA CGACAGTCTT TCTCAGAGCT CAGAACTCAG
 301 AATTCGTTCT GGGCACTGTT AGTCGGGATC CTGAAGGGCT ACCAGCTCTT ACTAAGGAAG
 361 AATTTGACAC ACTAGTACGT AGGTATTGCT TATACTACCT TGGATTAGGC TTTGCTATGT
 421 TTGCAACATC TTATATACAG ATTGTGTGTT GGGAGACGTT CGCCGAACGA ATTACCCATA
 481 AATTACGAAA AATTTATCTA AAAGCCATAC TTCGGCAGCA GATCTCATGG TTTGACATTC
 541 AACAAACAGG AAATCTCACA GCTCGTCTAA CCGATGATCT CGAACGTGTT CGTGAAGGAC
 601 TTGGTGATAA ACTGTCGCTT TTTATACAAA TGGTGTCTGC TTTTGTGGCT GGTTTCTGTG
 661 TAGGATTCGC GTATAGCTGG TCAATGACGC TCGTGATGAT GGTCGTGGCG CCGTTTATAG
 721 TTATTTCTGC TAATTGGATG TCAAAAATCG TTGCTACTAG GACCCAAGTT GAACAGGAAA
 781 CCTACGCTGT TGCCGGTGCT ATAGCGGAGG AGACTTTCTC ATCGATACGA ACCGTACACT
 841 CGATATGTGG CCATAAAAGA GAGCTAACAA GATTTGAGGC AGCGTTGGAG AAAGGACGTC
 901 AGACAGGCCT TGTCAAATAT TTCTATATGG GTGTTGGTGT GGGATTTGGT CAGATGTGTA
 961 CCTATGTGTC CTACGCCTTG GCTTTTTGGT ATGGCAGTGT ACTGATCATC AACGACCCTG
1021 CATTGGATCG TGGCCGAATT TTCACAGTCT TTTTTGCTGT GATGTCCGGC TCAGCAGCTC
1081 TCGGCACATG TCTGCCACAT CTTAACACCA TATCCATCGC TCGAGGAGCG GTACGAAGTG
1141 TACTGTCAGT GATTAATAGT CGTCCAAAAA TCGATCCCTA TTCGTTAGAT GGCATTGTGC
1201 TCAACAATAT GAGAGGATCT ATCCGCTTCA AGAACGTGCA TTTCTCCTAT CCTTCCCGAA
1261 GAACATTGCA GATATTGAAA GGTGTGTCAC TGCAAGTGTC GGCTGGCCAA AAAATTGCTT
1321 TGGTGGGTTC AAGCGGTTGT GGAAAGTCAA CGAACGTCAA TTTATTATTG AGATTTTATG
1381 ATCCGACAAG GGGAAAGGTA ACCATAGATG ATATTGATGT GTGTGATCTC AACGTGCAAA
1441 AACTTCGTGA ACAAATCGGT GTTGTTAGTC AGGAACCAGT GCTTTTCGAT GGCACACTAT
1501 TCGAAAATAT CAAGATGGGT TATGAACAGG CCACAATGGA GGAGGTCCAA GAAGCGTGCC
1561 GTGTGGCGAA TGCTGCCGAC TTCACCAAAC GACTTCCAGA AGGTTACGGC ACCCGAGTTG
1621 GTGAACGTGG TGTGCAGTTA AGTGGCGGAC AAAAGCAGCG AATTGCCATA GCTCGTGCGA
1681 TCATCAAGAA CCCTCGCATA CTGCTGCTCG ATGAAGCCAC CAGTGCTCTA GACACAGAAG
1741 CGGAATCAAT CGTGCAAGAG GCTCTGGAGA AGGCTCAAAA AGGGAGAACA ACCGTCATTG
1801 TAGCGCATCG TCTGTCTACT ATCAGAAACG TGGATCAGAT TTTCGTTTTC AAGAACGGAA
1861 CGATCGTTGA GCAGGGCACT CATGCCGAGT TGATGAACAA ACGTGGAGTA TTCTTTGAAA
1921 TGACTCAAGC ACAAGTCCTC CGACAAGAGA AGGAAGAGGA AGTTTTAGAT AGCGATGCGG
1981 AATCCGATGT CGTGTCACCG GATATTGCAT TACCCCATCT TAGTTCACTT CGATCCCGTA
2041 AAGAATCCAC AAGAAGTGCT ATCTCCGCGG TCCCCAGCGT TCAAGTATG CAAATCGAAA
2101 TGGAGGACCT TCGTGCCAAA CCAACTCCAA TGTCGAAAAT TTTCTATTTT AACCGTGACA
2161 AATGGGGATA TTTCATTTTG GGACTCATCG CCTGTATTAT TACTGGAACT GTTACACCGA
2221 CATTTGCAGT TTTATATGCG CAGATCATAC AGGTATACTC GGAACCTGTT GATCAAATGA
2281 AAGGCCATGT GCTGTTCTGG TGTGGAGCTT TCATCGTCAT TGGTCTCGTA CACGCTTTTG
2341 CGTTCTTTTT CTCGGCTATT TGTTTGGAC GTTGCGGCGA AGCGTTAACG AAAAAATTAC
2401 GTTTCGAGGC GTTCAAGAAC CTTCTGCGAC AGAATGTGGG ATTCTACGAC GATATCCGAC
2461 ACGGTACCGG TAAACTCTGT ACGCGATTTG CTACAGATGC ACCCAATGTC CGATATGTGT
2521 TCACTCGACT TCCGGGTGTG CTTTCATCGG TGGTGACCAT AATTGGAGCT TTGGTTATTG
2581 GATTCATCTT CGGGTGGCAG CTGGCTTTGA TTCTTATGGT GATGGTACCG TTGATCATCG
2641 GTAGTGGATA CTTCGAGATG CGCATGCAGT TTGGTAAGAA GATGCGTGAC ACAGAGCTTC
2701 TTGAAGAGGC TGGGAAAGTT GCCTCTCAAG CCGTGGAGAA CATTCGTACC GTGCATGCCC
2761 TGAATAGGCA AGAGCAGTTC CATTTCATGT ATTGCGAGTA TTTGAAGGAA CCCTATCGAG
2821 AAAATCTTTG CCAGGCGCAC ACCTACGGGG GTGTATTCGC GTTCTCACAA TCGTTGTTAT
2881 TCTTTATGTA TGCTGTAGCA TTTTGGATTG GTGCAATCTT CGTGACAACA CACAGCATGC
2941 AACCGATTGA CGTTTACCGA GTATTTTTCG CGTTCATGTT TTGTGGACAA ATGGTCGGCA
```

FIG. 4A

```
3001 ACATTTCTTC TTTTATTCCT GACGTTGTGA AAGCTCGCCT GGCTGCATCG CTCCTTTTCT
3061 ACCTTATCGA ACACCCATCA GAAATTGATA ATTTGTCCGA GGATGGTGTC ACGAAGAAAA
3121 TCTCTGGTCA TATCTCGTTC CGCAATGTCT ATTTCAATTA TCCGACAAGA AGACAGATCA
3181 GAGTACTCCG TGGACTTAAC CTAGAGATAA ATCCTGCAC GACGGTAGCG CTTGTTGGGC
3241 AGTCTGGTTG TGGAAAAAGC ACTGTGATGG CGTTGTTGGA ACGGTTTTAC AATCAAAACA
3301 AGGGCGTGAT TACGGTGGAC GGCGAAAACA TCAGAAACAT GAACATACGC AATCTTCGTG
3361 AGCAAGTGTG TATTGTTAGC CAGGAACCAA CGCTGTTCGA CTGTACCATC ATGGAAAACA
3421 TCTGTTACGG TCTCGATGAC CCCAAGCCGT CCTACGAACA GGTTGTTGCT GCAGCAAAAA
3481 TGGCGAACAT TCACAATTTT GTGCTGGGAC TACCAGAGGG TTACGATACG CGTGTTGGTG
3541 ARAAAGGCAC TCAGCTGTCA GGCGGACAGA AGCAACGAAT AGCCATAGCC AGAGCGCTGA
3601 TTCGAGATCC GCCTATACTT CTGCTGGATG AGGCGACAAG CGCGCTGGAT ACCGAGAGTG
3661 AAAAGATCGT GCAAGACGCC CTAGAGGTTG CTCGCCAAGG TAGAACGTGC CTTGTAATTG
3721 CCCATCGCCT TTCTACAATT CAAGACAGTG ACGTCATAGT GATGATCCAG GAGGGGAAAG
3781 CTACAGACAG AGGCACTCAT GAACATTTAC TGATGAAGAA CGATCTATAC AAACGGCTAT
3841 GCGAAACACA ACGACTCGTT GAATCACAAT GAGTTTTTAG TGCCAATCGA TAGTGATCGA
3901 TAAGCTATGG ATTAGTCTTT AACACTTACT GATCATATGA CTCTATCTCG TGCTTTATTA
3961 TAATGTACAT ATGTAATGGT TTTGATCTTA CATATCTTGT AATTGGTCCT CACTATCATA
4021 ATGCCTTTAG TAGTATATTA ACAGTTTTAT TAATACAACT TAAGTAACAT ATTAACAATT
4081 TTATTAATAT AACTTAAGTA AGATATTGAC AGTTTTATTA ATTGGAGGA TTTATAATAA
4141 AACCTCGTGC CGCTCGTGCC GAAACGATAT CAAGC
```

FIG. 4B

```
   1 GGTTTAATTA CCCAAGTTTG AGAGATCGTT CTCAAGCTGG TAAAATGTTC GAAAAAGGCC
  61 AAGATGATGA ACGTATACCA TTACTCGGTT CATCCAAGAA AAGTTCAATC GGCGAAGTCA
 121 GTAAAAAAGA AGAACCGCCT ACAATAACAA ACCGTGGAAT TCTCTCCTTA GCCACTACAT
 181 TGGATTATGT GCTTCTTGCG GCTGGTACGC TGGCGCCGTG TGTTCATGGC GCTGGATTCT
 241 CAGTACTCGG TATTGTACTC GGTGGTATGA CGACAGTCTT TCTCAGAGCT CAGAACTCAG
 301 AATTCGTTCT GGGCACTGTT AGTCGGGATC CTGAAGGGCT ACCAGCTCTT ACTAAGGAAG
 361 AATTTGACAC ACTAGTACGT AGGTATTGCT TATACTACCT TGGATTAGGC TTTGCTATGT
 421 TTGCAACATC TTATATACAG ATTGTGTGTT GGGAGACGTT CGCCGAACGA ATTACCCATA
 481 AATTACGAAA AATTTATCTA AAAGCCATAC TTCGGCAGCA GATCTCATGG TTTGACATTC
 541 AACAAACAGG AAATCTCACA GCTCGTCTAA CCGATGATCT CGAACGTGTT CGTGAAGGAC
 601 TTGGTGATAA ACTGTCGCTT TTTATACAAA TGGTGTCTGC TTTTGTGGCT GGTTTCTGTG
 661 TAGGATTCGC GTATAGCTGG TCAATGACGC TCGTGATGAT GGTCGTGGCG CCGTTTATAG
 721 TTATTTCTGC TAATTGGATG TCAAAAATCG TTGCTACTAG GACCCAAGTT GAACAGGAAA
 781 CCTACGCTGT TGCCGGTGCT ATAGCGGAGG AGACTTTCTC ATCGATACGA ACCGTACACT
 841 CGATATGTGG CCATAAAAGA GAGCTAACAA GATTTGAGGC AGCGTTGGAG AAAGGACGTC
 901 AGACAGGCCT TGTCAAATAT TTCTATATGG GTGTTGGTGT GGGATTTGGT CAGATGTGTA
 961 CCTATGTGTC CTACGCCTTG GCTTTTTGGT ATGGCAGTGT ACTGATCATC AACGACCCTG
1021 CATTGGATCG TGGCCGAATT TTCACAGTCT TTTTTGCTGT GATGTCCGGC TCAGCAGCTC
1081 TCGGCACATG TCTGCCACAT CTTAACACCA TATCCATCGC TCGAGGAGCG GTACGAAGTG
1141 TACTGTCAGT GATTAATAGT CGTCCAAAAA TCGATCCCTA TTCGTTAGAT GGCATTGTGC
1201 TCAACAATAT GAGAGGATCT ATCCGCTTCA AGAACGTGCA TTTCTCCTAT CCTTCCCGAA
1261 GAACATTGCA GATATTGAAA GGTGTGTCAC TGCAAGTGTC GGCTGGCCAA AAAATTGCTT
1321 TGGTGGGTTC AAGCGGTTGT GGAAAGTCAA CGAACGTCAA TTTATTATTG AGATTTTATG
1381 ATCCGACAAG GGGAAAGGTA ACCATAGATG ATATTGATGT GTGTGATCTC AACGTGCAAA
1441 AACTTCGTGA ACAAATCGGT GTTGTTAGTC AGGAACCAGT GCTTTTCGAT GGCACACTAT
1501 TCGAAAATAT CAAGATGGGT TATGAACAGG CCACAATGGA GGAGGTCCAA GAAGCGTGCC
1561 GTGTGGCGAA TGCTGCCGAC TTCACCAAAC GACTTCCAGA AGGTTACGGC ACCCGAGTTG
1621 GTGAACGTGG TGTGCAGTTA AGTGGCGGAC AAAAGCAGCG AATTGCCATA GCTCGTGCGA
1681 TCATCAAGAA CCCTCGCATA CTGCTGCTCG ATGAAGCCAC CAGTGCTCTA GACACAGAAG
1741 CGGAATCAAT CGTGCAAGAG GCTCTGGAGA AGGCTCAAAA AGGGAGAACA ACCGTCATTG
1801 TAGCGCATCG
```

FIG. 5

```
   1 AGTGCTTTTC GATGGCACAC TATTCGAAAA TATCAAGATG GGTTATGAAC AGGCCACAAT
  61 GGAGGAGGTC CAAGAAGCGT GCCGTGTGGC GAATGCTGCC GACTTCACCA AACGACTTCC
 121 AGAAGGTTAC GGCACCCGAG TTGGTGAACG TGGTGTGCAG TTAAGTGGCG GACAAAAGCA
 181 GCGAATTGCC ATAGCTCGTG CGATCATCAA GAACCCTCGC ATACTGCTGC TCGATGAAGC
 241 CACCAGTGCT CTAGACACAG AAGCGGAATC AATCGTGCAA GAGGCTCTGG AGAAGGCTCA
 301 AAAAGGGAGA ACAACCGTCA TTGTAGCGCA TCGTCTGTCT ACTATCAGAA ACGTGGATCA
 361 GATTTTCGTT TTCAAGAACG GAACGATCGT TGAGCAGGGC ACTCATGCCG AGTTGATGAA
 421 CAAACGTGGA GTATTCTTTG AAATGACTCA AGCACAAGTC CTCCGACAAG AGAAGGAAGA
 481 GGAAGTTTTA GATAGCGATG CGGAATCCGA TGTCGTGTCA CCGGATATTG CATTACCCCA
 541 TCTTAGTTCA CTTCGATCCC GTAAAGAATC CACAAGAAGT GCTATCTCCG CGGTCCCCAG
 601 CGTTCGAAGT ATGCAAATCG AAATGGAGGA CCTTCGTGCC AAACCAACTC CAATGTCGAA
 661 AATTTTCTAT TTTAACCGTG ACAAATGGGG ATATTTCATT TTGGGACTCA TCGCCTGTAT
 721 TATTACTGGA ACTGTTACAC CGACATTTGC AGTTTTATAT GCGCAGATCA TACAGGTATA
 781 CTCGGAACCT GTTGATCAAA TGAAAGGCCA TGTGCTGTTC TGGTGTGGAG CTTTCATCGT
 841 CATTGGTCTC GTACACGCTT TTGCGTTCTT TTTCTCGGCT ATTTGTTTGG GACGTTGCGG
 901 CGAAGCGTTA ACGAAAAAAT TACGTTTCGA GGCGTTCAAG AACCTTCTGC GACAGAATGT
 961 GGGATTCTAC GACGATATCC GACACGGTAC CGGTAAACTC TGTACGCGAT TTGCTACAGA
1021 TGCACCCAAT GTCCGATATG TGTTCACTCG ACTTCCGGGT GTGCTTTCAT CGGTGGTGAC
1081 CATAATTGGA GCTTTGGTTA TTGGATTCAT CTTCGGGTGG CAGCTGGCTT TGATTCTTAT
1141 GGTGATGGTA CCGTTGATCA TCGGTAGTGG ATACTTCGAG ATGCGCATGC AGTTTGGTAA
1201 GAAGATGCGT GACACAGAGC TTCTTGAAGA GGCTGGGAAA GTTGCCTCTC AAGCCGTGGA
1261 GAACATTCGT ACCGTGCATG CCCTGAATAG GCAAGAGCAG TTCCATTTCA TGTATTGCGA
1321 GTATTTGAAG GAACCCTATC GAGAAAATCT TTGCCAGGCG CACACCTACG GGGTGTATT
1381 CGCGTTCTCA CAATCGTTGT TATTCTTTAT GTATGCTGTA GCATTTTGGA TTGGTGCAAT
1441 CTTCGTGGAC AACCACAGCA TGCAACCGAT TGACGTTTAC CGAGTATTTT TCGCGTTCAT
1501 GTTTTGTGGA CAAATGGTCG GCAACATTTC TTCTTTTATT CCTGACGTTG TGAAAGCTCG
1561 CCTGGCTGCA TCGCTCCTTT TCTACCTTAT CGAACACCCA TCAGAAATTG ATAATTTGTC
1621 CGAGGATGGT GTCACGAAGA AAATCTCTGG TCATATCTCG TTCCGCAATG TCTATTTCAA
1681 TTATCCGACA AGAAGACAGA TCAGAGTACT CCGTGGACTT AACCTAGAGA TAAATCCTGG
1741 CACGACGGTA GCGCTTGTTG GGCAGTCTGG TTGTGGAAAA AGCACTGTGA TGGCGTTGTT
1801 GGAACGGTTT TACAATCAAA ACAAGGGCGT GATTACGGTG GACGGCGAAA ACATCAGAAA
1861 CATGAACATA CGCAATCTTC GTGAGCAAGT GTGTATTGTT AGCCAGGAAC CAACGCTGTT
1921 CGACTGTACC ATCATGGAAA ACATCTGTTA CGGTCTCGAT GACCCCAAGC CGTCCTACGA
1981 ACAGGTTGTT GCTGCAGCAA AAATGGCGAA CATTCACAAT TTTGTGCTGG ACTACCAGA
2041 GGGTTACGAT ACGCGTGTTG GTGARAAAGG CACTCAGCTG TCAGGCGGAC AGAAGCAMCG
2101 AATAGCCATA GCCAGAGCGC TGATTCGAGA TCCGCCTATA CTTCTGCTGG ATGAGGCGAC
2161 AAGCGCGCTG GATACCGAGA GTGAAAAGAT CGTGCAAGAC GCCCTAGAGG TTGCTCGCCA
2221 AGGTAGAACG TGCCTTGTAA TTGCCCATCG CCTTTCTACA ATTCAAGACA GTGACGTCAT
2281 AGTGATGATC CAGGAGGGGA AAGCTACAGA CAGAGGCACT CATGAACATT TACTGATGAA
2341 GAACGATCTA TACAAACGGC TATGCGAAAC ACAACGACTC GTTGAATCAC AATGAGTTTT
2401 TAGTGCCAAT CGATAGTGAT CGATAAGCTA TGGATTAGTC TTTAACACTT ACTGATCATA
2461 TGACTCTATC TCGTGCTTTA TTATAATGTA CATATGTAAT GGTTTTGATC TTACATATCT
2521 TGTAATTGGT CCTCACTATC ATAATGCCTT TAGTAGTATA TTAACAGTTT TATTAATACA
2581 ACTTAAGTAA CATATTAACA ATTTTATTAA TATAACTTAA GTAAGATATT GACAGTTTTA
2641 TTAATTTGGA GGATTTATAA TAAAACCTCG TGCCGCTCGT GCCGAAACGA TATCAAGC
```

FIG. 6

```
   1 MFEKGQDDER IPLLGSSKKS SIGEVSKKEE PPTITNRGIL SLATTLDYVL LAAGTLAPCV
  61 HGAGFSVLGI VLGGMTTVFL RAQNSEFVLG TVSRDPEGLP ALTKEEFDTL VRRYCLYYLG
 121 LGFAMFATSY IQIVCWETFA ERITHKLRKI YLKAILRQQI SWFDIQQTGN LTARLTDDLE
 181 RVREGLGDKL SLFIQMVSAF VAGFCVGFAY SWSMTLVMMV VAPFIVISAN WMSKIVATRT
 241 QVEQETYAVA GAIAEETFSS IRTVHSICGH KRELTRFEAA LEKGRQTGLV KYFYMGVGVG
 301 FGQMCTYVSY ALAFWYGSVL IINDPALDRG RIFTVFFAVM SGSAALGTCL PHLNTISIAR
 361 GAVRSVLSVI NSRPKIDPYS LDGIVLNNMR GSIRFKNVHF SYPSRRTLQI LKGVSLQVSA
 421 GQKIALVGSS GCGKSTNVNL LLRFYDPTRG KVTIDDIDVC DLNVQKLREQ IGVVSQEPVL
 481 FDGTLFENIK MGYEQATMEE VQEACRVANA ADFTKRLPEG YGTRVGERGV QLSGGQKQRI
 541 AIARAIIKNP RILLLDEATS ALDTEAESIV QEALEKAQKG RTTVIVAHRL STIRNVDQIF
 601 VFKNGTIVEQ GTHAELMNKR GVFFEMTQAQ VLRQEKEEEV LDSDAESDVV SPDIALPHLS
 661 SLRSRKESTR SAISAVPSVR SMQIEMEDLR AKPTPMSKIF YFNRDKWGYF ILGLIACIIT
 721 GTVTPTFAVL YAQIIQVYSE PVDQMKGHVL FWCGAFIVIG LVHAFAFFFS AICLGRCGEA
 781 LTKKLRFEAF KNLLRQNVGF YDDIRHGTGK LCTRFATDAP NVRYVFTRLP GVLSSVVTII
 841 GALVIGFIFG WQLALILMVM VPLIIGSGYF EMRMQFGKKM RDTELLEEAG KVASQAVENI
 901 RTVHALNRQE QFHFMYCEYL KEPYRENLCQ AHTYGGVFAF SQSLLFFMYA VAFWIGAIFV
 961 DNHSMQPIDV YRVFFAFMFC GQMVGNISSF IPDVVKARLA ASLLFYLIEH PSEIDNLSED
1021 GVTKKISGHI SFRNVYFNYP TRRQIRVLRG LNLEINPGTT VALVGQSGCG KSTVMALLER
1081 FYNQNKGVIT VDGENIRNMN IRNLREQVCI VSQEPTLFDC TIMENICYGL DDPKPSYEQV
1141 VAAAKMANIH NFVLGLPEGY DTRVGEKGTQ LSGGQKQRIA IARALIRDPP ILLLDEATSA
1201 LDTESEKIVQ DALEVARQGR TCLVIAHRLS TIQDSDVIVM IQEGKATDRG THEHLLMKND
1261 LYKRLCETQR LVESQ*
```

FIG. 7

```
   1 CCCGTTGTTG CCGGTGCTAT AGCGGAGGAG ACTTTCTCAT CGATACGAAC CGTACACTCG
  61 TTATGTGGCC ATAAAAGAGA GCTAACAAGG CAGCGTTGGA GAAAGGACGT CAGACAGGCC
 121 TTGTCAAATA TTTCTATATG GGTGTTGGTG TGAGATTTGG TCAGATGTGT ACCTATGTGT
 181 CCTACGCCTT GGCTTTTTGG TATGGCAGTG TACTGATCAT CAACGACCCT GCATTGGATC
 241 GTGGCCGAAT TTTCACAGTC TTTTTGCTGT GATGTCCGGC TCAGCAGCTC TCGGCACATG
 301 TCTGCCACAT CTTAACACCA TATCCATCGC TCGAGGAGCG GTACGAAGTG TACTGTCAGT
 361 GATTAATAGT CGTCCAAAAA TCGATCCCTA TTCGTTAGAT GGCATTGTGC TCAACAATAT
 421 GAGAGGATCT ATTCGCTTCA AGAACGTGCA TTTCTCCTAT CCTTCCCGAA GAACATTGCA
 481 GATATTGAAA GGTGTGTCAC TGCAAGTGTC GGCTGGCCAA AAAATTGCTT TGGTGGGTTC
 541 AAGCGGTTGT GGAAAGTCAA CGATCGTCAA TTTATTATTG AGATTTATG ATCCGACAAG
 601 GGGAAAGGTA ACCATAGATG ATATTGATGT GTGTGATCTC AACGTGCAAA AACTTCGTGA
 661 ACAAATCGGT GTTGTTAGTC AGGAACCAGT GCTTTTCGAT GGCACACTAT TCGAAAATAT
 721 CAAGATGGGT TATGAACAGG CCACAATGGA GGAGGTCCAA GAAGCGTGCC GTGTGGCGAA
 781 TGCTGCCGAC TTCATCAAAC GACTTCCAGA AGGTTACGGC ACCCGAGTTG GTGAACGTGG
 841 TGTGCAGTTA AGTGGCGGAC AAAAGCAGCG AATTGCCATA GCTCGTGCGA TCATCAAGAA
 901 CCCTCGCATA CTGCTGCTCG ATGAAGCCAC CAGTGCTCTA GACACAGAAG CGGAATCAAT
 961 CGTGCAAGAG GCTCTGGAGA AGGCTCAAAA AGGGAGAACA ACCGTCATTG TAGCGCATCG
1021 TCTGTCTACT ATCAGAAACG TGGATCAGAT TTTCGTTTTC AAGAACGGAA CGATCGTTGA
1081 GCAGGGCACT CATGCCGAGT TGATGAACAA ACGTGGAGTA TTCTTTGAAA TGACTCAAGC
1141 ACAAGTCCTC CGACAAGAGA AGGAAGAGGA AGTTTTAGAA AATACGGAAC CAGTAGCGAA
1201 GTGTCAAGAG GTATCCCTCC CTGCTCCTGA TGTCACTATT TTGGCTCCCC ATGAGGAACA
1261 ACCCGAGCTA CCTAGCCCGC CGGGTCGGTT AGAAAATACA AAGCAACATG AGCATCTCTG
1321 AATGTCTTTG TCTGAGATAC CGATGCGAA TCCGATGTCG TGTCACCGGA TATTGCATTA
1381 CCCCATCTTA GTTCACTTCG ATCCCGTAAA GAATCCACAA GAAGTGCTAT CTCCGCGGTC
1441 CCCAGCGTTC GAAGTATGCA AATCGAAATG GAGGACCTTC GTGCCAAACC AACTCCAATG
1501 TCGAAAATTT TCTATTTTAA CCGTGACAAA TGGGCATATT TCATTTTGGG ACTCATCGCC
1561 TGTATTATTA CTGGAACTGT TACACCGACA TTTGCAGTTT TATATGCGCA GATCATACAG
1621 GTATACTCGG AACCTGTTGA TCAAATGAAA GGCCATGTGC TGTTCTCGGTG TGGAGCTTTC
1681 ATCGTCATTG GTCTCGTACA CGCTTTTGCG TTCTTTTTCT CGGCTATTTG TTTGGGACGT
1741 TGCGGCGAAG CGTTAACGAA AAAATTACGT TTCGAGGCGT TCAAGAACCT TCTGCGACAG
1801 GATGTGGGAT TCTACGACGA TATCCGACAC GGTACCGGTA AACTCTGTAC GCGATTTGCT
1861 ACAGATGCAC CCAATGTCCG ATATGTGTTC ACTCGACTTC CGGGTGTGCT TTCATCGGTG
1921 GTGACCATAA TTGGAGCTTT GGTTATTGGA TTCATCTTCG GTGGCAGCT GGCTTTGATT
1981 CTTATGGTGA TGGTACCGTT GATCATCGGT AGTGGATACT TCGAGATGCG CATGCAGTTT
2041 GGTAAGGAGA TGCGTGACAC AGAGCTTCTT GAAGAGGCTG GGAAAGTTGC CTCTCAAGCC
2101 GTGGAGAACA TTCGTACCGT GCATGCCCTG AATAGGCAAG AGCAGTTCCA TTTCATGTAT
2161 TGCGAGTATT TGAAGGAACC CTATCGAGAA AATCTTTGCC AGGCGCACAC CTACGGGGGT
2221 GTATTCGCGT TCTCACAATC GTTGTTATTC TTTATGTATG CTGTAGCATT TTGGATTGGT
2281 GCAATCTTCG TGGACAACCA CAGCATGCAA CCGATTGACG TTTACCGAGT ATTTTCGCG
2341 TTCATGTTTT GTGGACAAAT GGTCGGCAAC ATTTCTTCTT TTATTCCTGA CGTTGTGAAA
2401 GCTCGCCTGG CTGCATCGCT CCTTTTCTAC CTTATCGAAC ACCCATCAGA AATTGATAAT
2461 TTGTCCGAGG ATGGTGTCAC GAAGAAAATC TCTGGTCATA TCTCGTTCCG CAATGTCTAT
2521 TTCAATTATC CGACAAGAAG ACAGATCAGA GTACTCCGTG GACTTAACCT AGAGATAAAT
2581 CCTGGCACGA AGGTAGCGCT TGTTGGGCAG TCTGGTTGTG GAAAAAGCAC TGTGATGGCG
2641 TTGTTGGAAC GGTTTTACAA TCAAAACAAG GGCGTGATTA CGGTGGACGG CGAAAACATC
2701 AGAAACATGA ACATACGCAA TCTTCGTGAG CAAGTGTGTA TTGTAAGCCA GGAACCAACG
2761 CTGTTCGACT GTACCATCAT GGAAAACATC TGTTACGGTC TCGATGACCC CAAGCCGTCC
2821 TACGAACAGG TTGTTGCTGC AGCAAAAATG GCGAACATTC ACAATTTTGT GCTGGGACTA
2881 CCAGAGGGTT ACGATACGCG TGTTGGTGAG AAAGGCACTC AGCTGTCAGG CGGACAGAAG
2941 CAACGAATAG CCATAGCCAG AGCGCTGATT CGAGATCCGC CTATACTTCT GCTGGATGAG
3001 GCGACAAGCG CGCTGGATAC CGAGAGTGAA AAGATCGTGC AAGACGCCCT AGAGGTTGCT
```

FIG. 8A

```
3061 CGCCAAGGTA GAACGTGCCT TGTAATTGCC CATCGCCTTT CTACAATTCA AGACAGTGAC
3121 GTCATAGTGA TGATCCAGGA GGGGAAAGCT ACAGACAGAG GCACTCATGA ACATTTACTG
3181 ATGAAGAACG ATCTATACAA ACGGCTATGC GAAACACAAC GACTCGTTGA ATCACAATGA
3241 GTTTTTAGTG CCAATCGATA GTGATCGATA AGCTATGGAT TAGTCTTTAA CACTTACTGA
3301 TCACAAATTT TATCTCGTGC TTTATTCTAA TGTACATATG TAACGGTTTT GATCTTACAT
3361 ATCTTGTAAT TGGTCCTCAC TATCATAATG CCTTTAGTAG TACATTAACA GTTTTATTAA
3421 TACAACTTAA GTAACATATT AACAATTTTA TTAATATAAC TTAAGTAAGA TATTGACAGT
3481 TTTATTAATT TGGAGGATTT ATAATAAAAC TT
```

FIG. 8B

```
   1 CCCGACTTCC GGAAGGTTAC GGCACCCGAG TAGGTGAACG TGGTGTACAA CTAAGTGGCG
  61 GACAAAAGCA GCGCATCGCT ATTGCTCGCG CCATCATTAA AAACCCTCGT ATACTTCTGC
 121 TTGACGAAGC CACCAGTGCT CTGGACACAG AGGCGGAATC AATTGTGCAA GAAGCTCTCG
 181 AGAAAGCTCA AAAAGGACGA ACGACCGTCA TTGTAGCGCA TCGCCTATCT ACCATCAGAA
 241 ATGTCGATCA AATTTTCGTC TTCAAGAATG AAACGATTGT TGAGCAGGGT ACACATGCAG
 301 AGTTGATGAA CAAACGAGGA GTGTTCTTTG AAATGACTCA AGCACAGGTC CTTCGACAAG
 361 AAAAGGAAGA GGAGGTCTTA GAAAATACGG AACCAGTAGC GAAGTGTCAA GAGGCATCCT
 421 TTCCTGCTCC TGATGTCACT ATTTTGACTC CCCATGACGA ACAACCCGAG CTACTTAGCC
 481 CGCCGGATAG CGATGCGGAA TCCGACGTCA TGTCACCGGA TCTTGGCTTA CCCCATCTTA
 541 GTTCACTTCG ATCACGTAAA GAGTCCACAA GAAGTGCTAT TTCCGCAGTC CCCAGCGTTC
 601 GGAGTATGCA GATCGAAATG GAGGACCTTC GTGCCAAACC GACTCCGATG TCGAAAATTT
 661 TCTATTTCAA CCGTGACAAA TGGGGATTTT TCATTTTGGG ACTCATCGCC TGTATTATAA
 721 CTGGAACTGT TACACCGACA TTTGCAGTTT TATATGCGCA GATCATACAG GTATACTCGG
 781 AACCTGTTGA TCAAATGAAA GGCCATGTGC TGTTTTGGTG TGGAGCTTTC ATCGTCATTG
 841 GTCTCGTACA CGCATTTGCG TTCTTTTTCT CGGCCATTTG TCTGGGACGT TGCGGCGAAG
 901 CTTTAACGAA GAAGTTACGT TTCGAGGCGT TCAAGAACCT TCTCCGACAA GATGTGGGAT
 961 TCTACGACGA TATCCGACAC GGTACCGGTA AACTCTGTAC GCGATTTGCT ACAGATGCAC
1021 CCAATGTTCG ATATGTGTTC ACTCGACTTC CGGGTGTACT TTCATCGGTG GTGACCATAA
1081 TCGGAGCTTT GGTTATTGGA TTTATTTTCG GGTGGCAGCT GGCCTTGATT CTTATGGTCA
1141 TGGTACCGTT GATCATTGGC AGTGGATACT TCGAGATGCG CATGCAGTTT GGTAAAAAGA
1201 TGCGTGACAC AGAGCTTCTT GAAGAGGCTG GGAAAGTTGC CTCACAAGCC GTAGAGAATA
1261 TTCGTACCGT ACATGCCCTG AATCGGCAAG AGCAGTTCCA TTTCATGTAC TGCGAGTATT
1321 TGAAGGAACC CTATCGAGAG AATCTTTGCC AGGCGCACAC TTACGGGGGT GTATTCGCGT
1381 TTTCACAGTC GTTGTTATTC TTTATGTATG CTGTAGCATT TTGGATTGGT GCAATCTTCG
1441 TGGACAACCA CAGCATGCAA CCGATTGATG TTTACCGAGT ATTTTTCGCG TTCATGTTTT
1501 GTGGACAAAT GGTTGGCAAC ATTTCGTCCT TCATCCCTGA TGTTGTGAAA GCTCGCCTGG
1561 CTGCATCGCT CCTTTTCTAC CTCATCGAAC ACCCATCAGA AATTGATAAC TTGTCCGAGG
1621 ATGGTGTCAA GAAGAAAATC TCTGGTCACA TCTCGTTCCG CAATGTCTAT TTCAATTACC
1681 CGACGAGAAG GCAGATCAGA GTACTCCGTG GACTTAACCT AGAGATAAAT CCTGGCACGA
1741 CGGTAGCGCT TGTTGGACAA TCTGGTTGTG GAAAAAGCAC TGTGATGGCG TTGTTGGAAC
1801 GCTTTTACAA TCAAAACAAG GGCGTGATTA CGGTTGACGG CGAAAACATC AGAAACATGA
1861 ACATACGCAA TCTCCGTGAG CAAGTATGTA TAGTCAGCCA GGAACCAACA CTGTTCGACT
1921 GTACCATCAT GGAAAACATC TGTTACGGAC TCGATGACCC CAAACCGTCC TACGAACAGG
1981 TTGTTGCGGC AGCAAAAATG GCGAACATCC ACAATTTTGT GCTGGGACTG CCAGAGGGTT
2041 ATGACACGCG TGTTGGCGAG AAAGGCACTC AGCTGTCAGG CGGACAAAAG CAAAGAATAG
2101 CCATAGCCCG AGCGCTGATC CGAGATCCGC CTATACTTCT GCTGGATGAG GCGACAAGCG
2161 CTCTGGACAC GGAGAGTGAG AAGATCGTGC AAGACGCCCT AGAGGTTGCT CGCCAAGGTA
2221 GAACGTGCCT TGTAATTGCC CACCGCCTTT CTACAATTCA AGACAGTGAC GTCATAGTGA
2281 TGATCCAGGA GGGAAAAGCT ACAGACAGAG CACTCATGA ACATTTACTG ATGAAGAACG
2341 ATCTATACAA ACGGCTATGC GAAACACAAC GACTCGTTGA ATCACAATGA GTTTTTAGTG
2401 CCGATCGATA GTGATCGATA AGCTATGGAT TAGTCTTCAA CACTTACTGA TCATATGACT
2461 ATCTCGTGCT TTATTATAAT GTACATATGT AATGGTTTTG ATGTAAGTTA AGTTATAATT
2521 GGTCTTCACT ATCATAATGC CTTTAGTAAT GCATTAACAC TTTTATAATA TAACTTGAAT
2581 AACATATTGA CAGTTTTATT AATATAACTT AAATAAGATA TTGACAGTTT TATTAATTTG
2641 GAGAATTTAT AATGAAACTT CTGGATTCCT GCAGCCCGGG G
```

FIG. 9

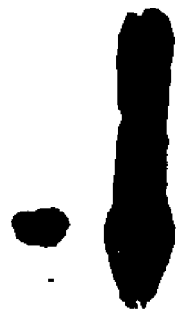
FIG. 10

5' GAAATGACTCAAGCACAAG 3' →

FIG. 12A

5' AGACAAAGACATTCAGAG 3' →

FIG. 12B

METHODS FOR DETECTING AND REVERSING RESISTANCE TO MACROCYCLIC LACTONE COMPOUNDS

RELATED U.S. APPLICATION DATA

This application is a division of U.S. application Ser. No. 09/749,340, filed Dec. 27, 2000, now U.S. Pat. No. 6,593,087, which is a division of U.S. application Ser. No. 09/067,676, filed Apr. 28, 1998, now U.S. Pat. No. 6,403,308, which claims the benefit, under 35 USC 119(e) of U.S. Provisional Application 60/045,160, filed Apr. 30, 1997, now abandoned.

BACKGROUND OF THE INVENTION

1. Field of the Invention

This invention relates generally to novel methods for diagnosing and overcoming resistance to the macrocyclic lactone compounds. More specifically, the invention pertains to unique methods for detecting the development of resistance to macrocyclic lactones using nucleic acid probes and enhancing the efficacy of the macrocyclic lactones using multidrug resistant reversing agents.

2. Description of Related Art

Macrocyclic lactone compounds such as the LL-F28249 compounds, the milbemycins and the avermectins are widely used for treatment of nematode and arthropod parasites. The highly active LL-F28249 family of compounds are natural endectocidal agents isolated from the fermentation broth of *Streptomyces cyaneogriseus* subsp. *noncyanogenus*. U.S. Pat. No. 5,106,994 and its continuation U.S. Pat. No. 5,169,956 describe the preparation of the major and minor components, LL-F28249α-λ. The LL-F28249 family of compounds further includes, but is not limited to, the semisynthetic 23-oxo derivatives and 23-imino derivatives of LL-F28249α-λ which are shown in U.S. Pat. No. 4,916,154. Moxidectin, chemically known as 23-(O-methyloxime)-LL-F28249α, is a particularly potent 23-imino derivative. Other examples of LL-F28249 derivatives include, but are not limited to, 23-(O-methyloxime)-5-(phenoxyacetoxy)-LL-F28249α, 23-(semicarbazone)-LL-F28249α and 23-(thiosemicarbazone)-LL-F28249α.

The milbemycins, also known as the B-41 series of antibiotics, are naturally occurring macrocyclic lactones isolated from the microorganism, *Streptomyces hygroscopicus* subsp. *aureolacrimosus*. U.S. Pat. No. 3,950,360 shows the preparation of the macrolide antibiotics milbemycin$_{\alpha 1}$-$_{\alpha 10}$, milbemycin$_{\beta 1-\beta 3}$ etc. These compounds are also commonly referred to as milbemycin A, milbemycin B, milbemycin D and the like, or antibiotic B-41A1, antibiotic B-41A3, etc.

The avermectins, also known as the C-076 family of compounds, are naturally occurring macrocyclic lactones produced by the soil actinomycete microorganism, *Streptomyces avermitilis*. U.S. Pat. No. 4,310,519 discloses the isolation and preparation of the major components $A_{1a}$ (e.g., avermectin $A_{1a}$), $A_{2a}$, $B_{1a}$ and $B_{2a}$, and the minor components $A_{1b}$ (e.g., avermectin $A_{1b}$), $A_{2b}$, $B_{1b}$ and $B_{2b}$. The C-076 family additionally embraces the semisynthetic derivatives such as the 22,23-dihydroavermectins described in U.S. Pat. No. 4,199,569. The semisynthetic derivatives include, but are not limited to, ivermectin, abamectin, doramectin, eprinomectin and the like.

Resistance to all of the broad spectrum macrocyclic lactone compounds has been encountered in most regions of the world where the compounds are used routinely in animal production. For instance, drug resistance to ivermectin (IVM), chemically known as 22,23-dihydroavermectin $B_1$ or 22,23-dihydro C-076 $B_1$ and a commonly used member of the avermectin drug family, has become a widespread problem, particularly in nematodes of sheep, goats and cattle (Shoop, *Parasitol. Today* 9: 154-159, 1993). In some parts of the world, the survival of commercial animal production is threatened by the development of anthelmintic resistance. Additionally, there is conflicting evidence as to whether ivermectin (avermectin) resistance confers resistance to the related milbemycins or other macrolides (Arena et al., *J. Parasitol.* 81: 286-294, 1995; Oosthuizen and Erasmus, *J. So. African Vet. Assoc.* 64: 9-12, 1993; Pomroy and Whelan, *Vet. Rec.* 132: 416, 1993; Shoop, 1993; Condora et al., *Vet. Rec.* 132: 651-652, 1993; Pomroy et al., *N.Z. Vet. J.* 40: 76, 1992; Pankavich et al., *Vet. Rec.* 130: 241-242, 1992; Craig et al., *Vet. Parasitol.* 41: 329-333, 1992). The mechanisms of resistance to the avermectins, the milbemycins and other macrocyclic lactone compounds remain unknown.

P-glycoproteins (Pgp) were identified some years ago as proteins involved in multidrug resistance (MDR) of mammalian tumor cells (Julino and Ling, 1976; Gros and Buschman, 1993; Gotteesman and Pastan, 1993). MDR proteins may also be involved in drug resistance in the protozoal parasites *Entamoeba histolytica* (Whirth, *Archivos De Investigacion Medica* 21(Supp. 1): 183-189, 1990; Samuelson et al., *Mol. Biochem. Parasitol.* 38: 281-290, 1990), *Leishmania enriietti* (Chow, *Mol. Biochem. Parasitol.* 60: 195-208, 1993), *L. dononani* (Callahan et al., *Mol. Biochem. Parasitol.* 68: 145-149, 1994); and *Plasmodium falciparum* (Volkman et al., *Mol. Biochem. Parasitol.* 57: 203-211, 1993; Cowman et al., *J. Cell Biol.* 113: 1033-1042, 1991). While many researchers believe that the proposed mechanism for Pgp involvement in drug resistance is that Pgp behaves as a pump to increase drug efflux, Callahan et al. (1994) suggested that Pgp may work by decreasing drug influx. However, the whole picture of how Pgp can be responsible for drug resistance is still unclear.

Only recently have Pgp homologs been investigated in nematodes (Sangster, *Parasitol. Today* 10: 319-322, 1994; Lincke et al., *EMBO J.* 12: 1615-1620, 1993; Lincke et al., *J. Mol. Biol.* 228: 701-711, 1992). Three full length Pgp genes and one partial Pgp gene from the free-living nematode, *Caenorhabditis elegans* have been cloned, sequenced and mapped to chromosomes I, IV and X (Lincke et al., 1992). Sangster et al., *J. Cell Biochem.* 17 (Supp.): 1223, 1993, indicated evidence for several partial genes for Pgp in the parasitic nematode *Haemonchus contortus*, although sequence information was missing. In vivo experiments have shown that disruption of the mouse mdr1, a P-glycoprotein gene, leads to an impairment in the blood-brain barrier and to increased sensitivity to drugs in these mice (Schinkel et al., *Cell* 77:491-502, 1994). Mice with deletion of mcdr1a were 50-100 times more sensitive to ivermectin than normal mice.

Drug resistance based on overexpression of P-glycoprotein has been shown to be reversed by verapamil and a number of other calcium channel blockers, calmodulin antagonists, steroids and hormonal analogs, cyclosporins, dipyridamole and other MDR-reversing agents (Ford, *Hematol. Oncol. Clin. North Am.* 9: 337-361, 1995). However, there has been no report or suggestion in the literature to use MDR-reversing agents to combat resistance in nematodes and arthropods to pesticides.

There is a definite need to understand the mechanism of macrocyclic lactone resistance, to be able to detect insipient resistance before it becomes flagrant and is difficult to manage the health of the animals. The ability to reverse the resistance has great potential for maintaining parasite control in the face of a failure of conventional treatment. An important object of the present invention, thus, is to determine these mechanisms of resistance in order to find viable, sensitive means to detect and to overcome the problematic resistance thereby improving parasite control.

BRIEF SUMMARY OF THE INVENTION

Heretofore unknown, it is now found that the mechanism of resistance to the macrocyclic lactone compounds is due to overexpression of novel P-glycoprotein homologs. It is further newly found that the nucleic acid molecules encoding the P-glycoprotein homologs or the fragments thereof regulating this resistance are useful as unique probes in methods for diagnosing the resistance to the macrocyclic lactones. For the first time, the reversal of resistance to the macrocyclic lactone compounds using multidrug resistance reversing agents is described herein.

BRIEF DESCRIPTION OF THE DRAWINGS

The background of the invention and its departure from the art will be further described hereinbelow with reference to the accompanying drawings, wherein:

FIGS. 2A and 2B represent, respectively, the nucleotide sequence of the 432 bp PCR product shown in FIG. 1 and the predicted amino acid translation of the cDNA (which correspond to SEQ ID NO:1 and SEQ ID NO:2, respectively).

FIGS. 4A to 4B represent the full-length cDNA sequence (4175 bp) of the PGP-A clone from the *H. contortus* cDNA library with high homology to known P-glycoproteins (which corresponds to SEQ ID NO:3).

FIG. 5 represents the partial cDNA sequence (1810 bp) of the 5' end of the PGP-A clone from the *H. contortus* cDNA library (which corresponds to SEQ ID NO:4).

FIG. 6 represents the partial cDNA sequence (2698 bp) of the 3' end of the PGP-A clone from the *H. contortus* cDNA library (which corresponds to SEQ ID NO:5).

FIG. 7 represents the putative amino acid translation (1275 a.a.) of PGP-A cDNA (which corresponds to SEQ ID NO:6).

FIGS. 8A to 8B represent the partial cDNA sequence (3512 bp) of the 3' end of the related but different PGP-O clone from the *H. contortus* cDNA library (which corresponds to SEQ ID NO:7).

FIG. 9 represents the partial cDNA sequence (2681 bp) of 3' end of the related but different PGP-B clone from the *H. contortus* cDNA library (which corresponds to SEQ ID NO:8).

FIG. 10 shows the autoradiographs of the Southern blots of genomic DNA extracted from eggs of ivermectin sensitive and resistant strains of *H. contortus* (MKIS AND MKIR) after digestion with PvuII, electrophoresis and probed with the [$^{32}$P]-432 bp *H. contortus* Pgp probe.

FIGS. 12A and 12B represent the nucleic acid sequences comprising sense primer PGP2S (FIG. 12A, which corresponds to SEQ ID NO:9) and antisense primer PGPAS (FIG. 12B, which corresponds to SEQ ID NO:10) which are constructed from the nematode P-glycoprotein homolog cDNA clone PGP-O-3' (53 bp intron region) and are used to generate PCR products that are diagnostic for macrocyclic lactone endectocide resistance.

FIG. 16A) or ivermectin (IVM; FIG. 16B) with verapamil (VRP) against *H. contortus* moxidectin-resistant strain in jirds.

DETAILED DESCRIPTION OF THE INVENTION

Figure 1:
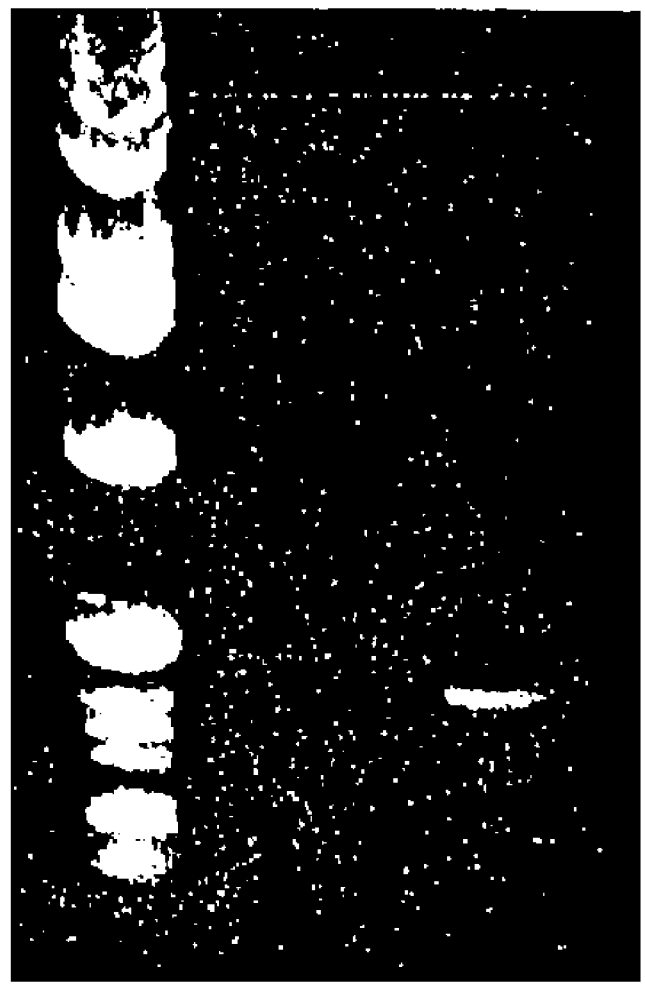
FIG. 1 shows the 432 bp PCR product which is generated from a *Haemonchus contortus* cDNA pBLUESCRIPT® library as template and degenerate primers based on the conserved ATP binding domains of *Caenorhabditis elegans* P-glycoprotein genes after electrophoresis on an agarose gel.

In accordance with the present invention, there are provided novel purified and isolated nucleic acid molecules encoding new P-glycoprotein homologs or the fragments thereof which regulate the macrocyclic lactone resistance. These nucleic acids find use as probes in innovative methods for the early diagnosis of a developing resistance to the endectocides. In the past, there have been no DNA or RNA based methods of detection of macrocyclic lactone resistance available. Now, the present invention uniquely provides the genetic basis of the resistance and the diagnosis of resistance using nucleic acid probes. The early detection under the guidance of this invention allows for maintaining adequate control of parasites and maintaining the usefulness of the macrocyclic lactone compounds. Additionally, the mechanism of resistance to macrocyclic lactones can be used in development of screens for identifying new anti-parasitic agents.

The novel methods of the present invention which are useful for detecting the resistance to macrocyclic lactone compounds in nematodes or arthropod pests utilize the new nucleic acid probes described herein. A variety of techniques well-known to those versed in the art can be employed for the analysis. Desirably, the method detects changes in genomic DNA or mRNA to provide a viable means for diagnosis of macrocyclic lactone resistance.

These methods include, for example, Polymerase Chain Reaction (PCR), hybridization in a Southern blot, Dot blot or Northern blot analysis or the use of an antibody to a sequence of peptides corresponding to the translation of the nucleotide sequences between the novel primers of the invention of an individual pest or mixture of the pests such as worms, using primers or probes, for example, corresponding to the portion of the cDNA sequence of PGP-O between the sequences identified as PGP2S and PGPAS (see FIGS. 12A and 12B). Alternative primers or probes within this region which can be utilized in the methods of the invention include, but are not limited to, all combinations of PCR primers or probes within this region or that of other PGP homolog sequences such as PGP-A, PGP-B, PGP-O and the like. Basically, the coding region of the P-glycoprotein homolog genes corresponding to the cDNA sequences identified as PGP-A, PGP-A-3', PGP-B, PGP-B-3', PGP-O, PGP-O-3' and the like is detected by PCR, Southern blot, Dot blot, Northern blot, Restriction Fragment Length Polymorphism (RFLP) and other standard means of analysis. Surprisingly, it has been found that the digestion pattern from the PCR fragment, the blot data or the antibody-antigen reaction are associated with susceptible or resistant traits which are diagnostic for the development of macrocyclic lactone resistance.

Polymerase Chain Reaction (PCR) can be employed for the detection of resistance to the macrocyclic lactone compounds by synthesizing a nucleic acid product which can be probed in conjunction with the Southern blot analysis or initially digested with a restriction enzyme for RFLP analysis as described herein. The primers are used to initiate a PCR reaction using the nucleic acids extracted from the pest specimen. They are used to synthesize a P-glycoprotein sequence or sequences. The PCR products can then be cut with restriction enzymes and the digested sequences run on an electrophoresis gel. Examples of suitable restriction enzymes that can be employed in the digestion of the PCR products include, but are not limited to, AluI, DdeI, HinfI, RsaI and the like. The pattern of bands observed on a Southern blot or a Northern blot indicates which P-glycoprotein alleles are present in a pest specimen such as the worm or group of worms. Some of the alleles can be associated with macrocyclic lactone sensitivity and others with resistance to macrocyclic lactones. The PCR products, followed by restriction enzyme digests, provide viable means for the detection of resistance. The process of cutting the PCR products or the nucleic acids such as DNA for the RFLP analysis greatly increases the sensitivity and specificity of the diagnosis.

Reverse Transcriptase-Polymerase Chain Reaction analysis (RT-PCR) can similarly be employed for the detection of resistance to the macrocyclic lactone compounds in nematode or arthropod pests. Typically, RNA from a nematode or arthropod specimen is extracted and reverse transcriptase followed by PCR, as described herein, is used to detect resistance.

By way of illustration, the nucleic acids, typically DNA for the PCR procedure or mRNA for RT-PCR, are extracted from the pest specimen, a pest known to be resistant to the macrocyclic lactone compounds and a pest known to be susceptible to the macrocyclic lactones. The nucleic acids derived from the resistant and the susceptible pests are used as a point of reference. The DNA, or cDNA produced by mRNA by Reverse Transcriptase, is denatured and the primers of the invention are added to form a mixture. The three mixtures are subjected to many cycles of PCR, usually digested by a restriction enzyme and subjected to gel electrophoresis. Subsequently, the pattern and the intensity of the bands from the specimen to that of the reference nucleic acids, i.e., DNA or cDNA, of the resistant and susceptible extracts are compared to detect the resistant population. Optionally, hybridization by a probe of the invention or use of a dye such as ethidium bromide to assist in visualizing the bands is included in the process.

Novel probes are used in the diagnosis of macrocyclic lactone resistance by detecting susceptibility or resistance to the macrocyclic lactones in the PCR assay. The primers which are used in the PCR assay are constructed, for example, from the nucleic acid sequences for the parasite P-glycoprotein homolog cDNA clones. Examples of suitable PCR primers that can be employed in the PCR analysis are the primers PGP2S and PGPAS used in the sense and antisense directions, respectively, which are constructed from PGP-O-3' or PGP-O (see FIGS. 12A and 12B). The primers can also be prepared from the full or partial sequences of other P-glycoprotein nucleic acids such as PGP-A, PGP-A-3', PGP-B-3', PGP-O, etc. and the complementary strands thereof which contain the region found to be diagnostic of macrocyclic lactone resistance. Alternative useful sequences can be obtained by conventional means such as hybridization techniques under standard or stringent conditions.

Southern blot, Dot blot or Northern blot may be prepared with the nucleic acid molecules from the nematode or the arthropod specimen and, using a probe comprising one of the nucleic acid molecule sequences encoding for resistance or portion thereof, one can compare the level of the nucleic acids extracted from the specimen to the level of the nucleic acids from the probe, for example, by measuring or detecting the level of DNA or mRNA. Generally, three nucleic acid extracts are mapped to make the comparison: from the pest specimen, from a pest known to be resistant and from a pest known to be susceptible. In the case of the Southern blot, the pattern of the bands is compared. With the Northern blot, either the pattern or the intensity of the bands is compared. For the Dot blot, the intensity of the spots is compared.

Another technique involves conducting a Restriction Fragment Length Polymorphism analysis (RFLP) by extracting the nucleic acids from a nematode or arthropod specimen, digesting the nucleic acid with a restriction enzyme, using a probe comprising one of the nucleic acid molecule sequences encoding for resistance or portion thereof and comparing the digestion pattern to that of the digestion pattern of nematodes or arthropods known to be from populations either resistant or sensitive to the macrocyclic lactone endectocides. When DNA is cut with the restriction enzyme, run on a gel and probed under the RFLP technique, the probe hybridizes with the similar sequences, but their length will vary depending upon where the restriction sites for that enzyme occurs. By repeating the analysis with DNA from individual worms, slightly different patterns are observed due to polymorphism. Specific patterns are diagnostic for the resistance gene. PvuII is an example of a preferred restriction enzyme that can be employed for RFLP analysis. Other conventional restriction enzymes known to those of ordinary skill in the art may be substituted in the method.

A further example of a process useful in the present invention for detecting resistance concerns making antibodies which employ the novel PGP protein homologs. For instance, an antibody may be prepared to a sequence of the peptide corresponding to the amino acid translation of the nucleic acids or the fragment thereof encoding the P-glycoprotein homologs which regulate resistance. Then, a specimen of the nematode or the arthropod pest, or the extract thereof, is prepared for reaction with the above antibody. The specimen or the extract is reacted with the antibody under suitable conditions that allow antibody-antigen binding to occur and, thereafter, the presence of the antibody-antigen binding is detected by conventional methods.

The above-described methods for the detection of resistance to the macrocyclic lactone compounds can optionally use a P-glycoprotein specific ligand or dye. Usually, the level of the P-glycoprotein in the specimen can more easily be observed using the ligand or dye and compared to the levels obtained in known macrocyclic lacrone resistant and susceptible populations of nematodes or arthropods. The ligand or dye is usually radiolabelled so that it can be readily detected. Examples of suitable ligands useful in this method include, but are not limited to, prazosin, azidoprazosin, iodoaryl-azidoprazosin and the like. A variety of conventional dyes may be employed such as, for instance, rhodamine 123, ethidium bromide and others.

For purposes of this invention, the nucleic acid molecule may be DNA, cDNA or RNA. However, in the most preferred embodiment of this invention, the nucleic acid probe is a cDNA molecule. Many of the foregoing methods illustrate extracted nucleic acids from *Haemonchus contortus*. It is contemplated that the present invention embraces the use of recombinant nucleic acids encoding for resistance or susceptibility to the macrolides as well as isolated nucleic acids from other worm strains or pest species.

The plasmids containing cDNA derived from *Haemonchus contortus* are deposited in connection with the present patent application and maintained pursuant to the Budapest Treaty in the American Type Culture Collection (ATCC), 10801 University Boulevard, Manassas, Va. 20110-2209, U.S.A. The cDNA sequences described herein are contained within plasmids (pBLUESCRIPT® II, commercially available from Stratagene Inc., La Jolla, Calif.) transformed into XLI-blue *Escherichia coli* bacterial strains. The plasmids identified as PGP-B-3', PGP-O-3' and PGP-A-5' have been deposited in the ATCC on Jan. 29, 1997 and have been assigned ATCC Designation Numbers 98307, 98309 and 98310, respectively. The plasmid PGP-A-3' has been deposited in the ATCC on Feb. 26, 1997 and has been assigned ATCC Designation Number 98336. It should be appreciated that other plasmids, which may be readily constructed using site-directed mutagenesis and the techniques described herein, are also encompassed within the scope of the present invention.

The present invention further relates to the unique reversal of resistance in parasites to the macrocyclic lactone compounds by administering or applying multidrug resistance reversing agents. This reversal of an existing resistance problem permits regaining satisfactory parasite control. The nematode or arthropod parasites or pests of this invention refer to crop insects, crop or mammalian nematodes, arthropod ectoparasites and endoparasites of mammals including acarids and the like.

Desirably, the multidrug resistance reversing agent is a calcium channel blocker such as verapamil, nifedipine and the like; a calmodulin antagonist such as trifluoperazine, prochlorperazine and the like; a vinca alkaloid analog such as vindoline, thaliblastine and the like; a steroidal agent such as progesterone and the like; a hormonal agent such as tamoxifen, estradiol and the like; an immunosuppressive agent such as cyclosporin A, SDZ-PSC 833 and the like, an antibiotic such as erythromycin, cefoperazone, ceftriaxone, tetracycline and the like; miscellaneous compounds such as dipyridamole, quinidine, reserpine, amiodarone, etc.; and other multidrug resistance reversing agents known to those versed in the art.

To increase the efficacy of the parasiticidal macrolides, the compounds of the invention are administered to mammals orally, parenterally, topically (local activity) or transdermally (systemic activity) depending upon the bioavailability of the selected medicinal by the desired route of administration. Parenteral administration of the medicinals encompasses any means other than orally, such as, for example, intravenously, intramuscularly, subcutaneously, intratracheally, intraruminally, etc. It is apparent that the MDR-reversing agents are administered in connection with the administration of the macrocyclic lactone compound encountering resistance in the nematodes or the arthropod ectoparasites or endoparasites of mammals. However, the administration of the MDR-reversing agents may be made either before or during concurrent administration of the macrocyclic lactones. If the MDR-reversing agent will be given before the endectocide, medical or veterinary personnel can readily determine by appropriate blood levels how far in advance the MDR-reversing agent may be given for increasing the macrolide's efficacy. Typically, the MDR-reversing agent will be administered within 24 hours of the start of endectocidal therapy and, preferably, within 4 hours before or concomitantly with administering the macrocyclic lactone.

In terms of dosage, the suitable amount of the MDR-reversing agent which is effective to increase the efficacy of the macrocyclic lactone compound against resistant nematodes or resistant arthropod ectoparasites or endoparasites will typically vary within a wide range of amounts at a variety of concentrations. The particular MDR-reversing agent selected for use with the specific endectocide will clearly affect the useful dose of the MDR-reversing agent. It is contemplated that selection of appropriate dosages of each MDR-reversing agent and the macrocyclic lactone compound to achieve the pesticidal enhancing effective amount can be easily titrated by routine testing known to those having ordinary skill in the medical and veterinary arts.

For use in parasiticidal treatment, the macrocyclic lactone compounds may be administered orally in a unit dosage form such as a capsule, a bolus or a tablet. The capsules and boluses comprise the active ingredient admixed with a conventional carrier vehicle such as starch, talc, magnesium stearate or dicalcium phosphate. The dry, solid unit dosage form are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be widely varied with respect to their total weight and content of the active agent depending upon factors such as the type and the weight of the mammal to be treated and the type and severity of the infection or infestation. Generally, the amount of the macrocyclic compound given in oral administration is about 0.001 mg to about 10 mg per kg of body weight and preferably, about 1 mg to about 5 mg per kg of body weight. However, the amount will vary depending upon the extent of the resistance already developed in the parasite.

For animals, the macrocyclic lactone compound and many of the MDR-reversing agents can also be administered via an animal feedstuff by intimately dispersing the active ingredient in the feed or using as a top dressing or in the form of pellets which may then be added to the finished feed or optionally fed separately. Suitable compositions include feed premixes or supplements in which the active compound is present in relatively large amounts, wherein said feed premixes or supplements are suitable for direct feeding to the animal or for addition to the feed either directly or after an intermediate dilution or blending step.

Typical carriers or diluents suitable for such compositions include distillers' dried grains, corn meal, citrus meal, fermentation residues, ground oyster shells, wheat products, molasses, corn cob meal, edible bean mill feed, soya grits, crushed limestone and the like. The active compounds are intimately dispersed throughout the carrier by methods such as grinding, stirring, milling or tumbling. Compositions containing about 0.005% to about 2.0%, by weight, of the active compound are particularly suitable as feed premixes.

Feed supplements, which are fed directly to the animal, contain about 0.0002% to 0.3%, by weight, of the active compounds. Such supplements are added to the animal feed in an amount to give the finished feed the concentration of active compound desired for the treatment or control of the resistant parasitic disease. Although the desired concentration of the active compound will vary depending upon a variety of factors such as the particular compound employed or the severity of the affliction, the macrocyclic compounds of this invention are usually fed at concentrations of about 0.00001% to about 0.02% in the feed.

Alternatively, the compounds of the present invention may be administered to the afflicted mammals parenterally, in which event the active ingredient is dissolved, dispersed or suspended in a sterile, isotonic, nontoxic liquid carrier vehicle. The active material is admixed with the nontoxic pharmaceutically acceptable vehicle, preferably a vegetable oil such as peanut oil, cotton seed oil or the like. Other parenteral vehicles such as propylene glycol, glycerol and the like may also be used for parenteral formulations.

In the parenteral formulations, the active macrolides are typically dissolved or suspended in the formulation in sufficient amount to provide from about 0.005% to about 5.0%, by weight, of the active compound in said formulation.

Conveniently, the macrolides may also be administered to the afflicted mammals by the topical or transdermal route to achieve either local or systemic effect. When used on animals, the compounds may be applied as a liquid drench. The animal drench is normally a solution, suspension or dispersion of the active compound, usually in water, together with a suspending agent such as bentonite and a wetting agent or similar excipient. Generally, the drenches also contain an antifoaming agent. Drench formulations typically contain about 0.001% to about 0.5%, by weight, of the active macrocyclic compound. Preferred drench formulations contain about 0.01% to about 0.1%, by weight.

Additionally, the macrocyclic compounds may be administered by applying as a gel, lotion, solution, cream or ointment to human skin or pouring on animal skin or hide via a solution. The topical or transdermal formulations comprise the active ingredient in combination with conventional inactive excipients and carriers. The cream, for example, may use liquid petrolatum, white petrolatum, propylene glycol, stearyl alcohol, cetyl alcohol, sodium lauryl sulfate, sodium phosphate buffer, polysorbates, parabens, emulsifying wax, polyoxyethylene-polyoxypropylene block copolymers, purified water and the like. Ointments, for example, may employ petrolatum, mineral oil, mineral wax, glycerin and the like. Topical solutions may provide the active ingredient compounded with propylene glycol, parabens, hydroxypropyl cellulose, preservatives. Pour-on formulations may constitute the active ingredient dissolved in a suitable inert solvent, such as dimethylsulfoxide, propylene glycol, butoxyethoxyethanol and the like. A particularly useful pour-on formulation comprises the active ingredient dissolved or dispersed in an aromatic solvent, PPG-2 myristyl ether propionate, polybutene, an antimicrobial agent, an antioxidant and a nontoxic pharmaceutically acceptable mineral or vegetable oil.

To increase the efficacy of the macrolides as pesticidal agents, the multidrug resistance reversing agents are applied to crops, crop seeds or the soil or water in which crops or seeds are growing or to be grown in a pesticidal enhancing effective amount. The MDR-reversing agents may be applied either before or concurrently with the application of the macrocyclic lactone. Typically, the MDR-reversing agent will be applied within 4 hours before or, preferably, concomitantly with the application of the macrocyclic lactone.

In terms of application rates, the suitable amount of the MDR-reversing agent which is effective to increase the efficacy of the macrocyclic lactone compound against resistant crop pests will typically vary within a wide range of amounts at a variety of concentrations and rates. The particular MDR-reversing agent selected for use with the crop pesticide will clearly affect the application rate of the MDR-reversing agent. It is contemplated that choice of appropriate amounts, concentrations, spray rates and the like of each MDR-reversing agent and the macrocyclic lactone compound to achieve the pesticidal enhancing effective amount can be easily determined by routine procedures known to those having ordinary skill in the agricultural art.

As insecticidal, nematocidal or acaricidal agents useful for protecting crop seeds or growing or harvested crops from the pest's attack, the compounds of the present invention may be formulated into dry compacted granules, flowable compositions, wettable powders, dusts, dust concentrates, microemulsions and the like, all of which lend themselves to soil, water or foliage application and provide the requisite plant protection. Such compositions include the compounds of the invention admixed with agronomically acceptable solid or liquid carriers.

In the agricultural composition, the active compounds are intimately mixed or ground together with the excipients and carriers in sufficient amounts to typically provide from about 3% to about 20% by weight of the macrocyclic lactone compound in said composition.

The compositions of this invention are useful in combatting agricultural pests that inflict damage upon crops while they are growing or while in storage. The compounds are applied using known techniques such as sprays, dusts, emulsions, wettable powders, flowables and the like to the growing or stored crops to provide protection against infestation by agricultural pests.

Unexpectedly, it is found that the mechanism of resistance to the macrocyclic lactone compounds is due to overexpression of novel P-glycoprotein homologs which causes an efflux of anthelmintic from the parasite. The present invention illustrates the involvement of the Pgp homolog genes in IVM resistance in *H. contortus*. The overexpression of Pgp-protein in IVM resistant strains of *H. contortus* is shown to be regulated by both rearrangement of genomic DNA encoding the PGP homologs and by gene transcription.

*H. contortus* in jirds (*Meriones unguiculatus*) has been used for the evaluation of anthelmintic efficacy and has been shown to correlate well with studies of this parasite in sheep (Conder et al., *J. Parasitol.* 78: 492-497, 1992). Employing the jird model, the present invention determines that multidrug reversing agents can unexpectedly be used to increase the efficacy of macrocyclic lactones against resistant parasites. As a representative example, the multidrug resistance (MDR) reversing agent verapamil (VRP) is shown to uniquely enhance the action of moxidectin and ivermectin against moxidectin susceptible and resistant *H. contortus*.

Parasites such as *H. contortus* contain Pgp homolog genes which are expressed in different stages of the parasite life cycle. This invention finds that the level of expression of P-glycoprotein is surprisingly elevated in different strains that are resistant to macrocyclic lactones such as ivermectin compared with the levels in the susceptible strains from which the resistant strains are derived. The higher level of Pgp expression, in ivermectin resistant strains, is associated with an alteration at the genomic level.

P-glycoproteins can act as molecular pumps to efflux hydrophobic xenobiotics from cells. An elevation in the level of the P-glycoproteins is the basis of multidrug resistance in cancer cells and also appears to be involved in some forms of drug resistance in some protozoa. An elevated level of Pgp has not so far been described as the mechanism of drug resistance in nematode parasites. This is the first evidence that shows that ivermectin resistance can be due to an elevation in P-glycoproteins. Ivermectin resistance is becoming a common problem in nematode parasites of animals and potentially in arthropod parasites. Its continued use against arthropods is likely to lead to the selection of similar resistance to that in nematodes.

Evidence exists that ivermectin shares a common action with other avermectins, such as doramectin, milbemycins (Arena et al., 1995) and moxidectin. It can be predicted that the development of resistance against other macrocyclic lactone compounds will involve hyperexpression of P-glycoprotein leading to elevated rates of drug efflux.

This work is significant because it allows the sensitive detection of ivermectin resistance and resistance to other macrocyclic lactone compounds in nematodes and arthropods using DNA and cDNA probes based on the demonstrated differences found in the PvuII digests of DNA from resistant and susceptible organisms. It also permits the prediction of the degree of resistance from the level of P-glycoprotein expression based on either Pgp mRNA or Pgp protein levels. This understanding of the mechanism of resistance to the macrolides allows active analogs to be synthesized which will remain effective in the presence of an mdr-based mechanism of resistance to other macrocyclic lactones. More specifically, chemicals which act on the mode of action receptor, the glutamate-gated chloride channel (Arena et al., 1995), but which are not efficiently effluxed by the P-glycoprotein pump, i.e., are poor substrates for Pgp efflux, can be selected to overcome resistance. This will lead to improvements in parasite controls, especially in the prevention and treatment of ivermectin resistance and cross-resistance to other avermectins, milbemycins and the LL-F28249 compounds.

This invention provides new evidence that in resistance to macrocyclic lactone endectocides, such as ivermectin, in nematode and arthropod parasites of animals, expression of P-glycoprotein is elevated compared with the level of expression in the parental susceptible strains of the parasite. It further shows that the higher level of expression is associated with differences, at the genomic level, of P-glycoprotein genes. For example, using Southern blot analysis of pooled DNA and by PCR (Polymerase Chain Reaction) analysis of individual worms, differences are determined in the genomic DNA for Pgp in *Haemonchus contortus* resistant to ivermectin compared with the susceptible parental strain, and the allele diversity for Pgp in resistant worms appears to be markedly reduced compared with the parental susceptible strain. Novel nucleic acid probes which can differentiate between susceptible and resistant parasites are now found and deemed to be useful in the early detection of the development of resistance to macrocyclic lactone compounds.

For the first time, this invention demonstrates that macrolactone resistance can be overcome by using a MDR-reversing agent. For example, verapamil, a well-known, relatively weak MDR-reversing agent, significantly increases the efficacy of moxidectin against moxidectin resistant *H. contortus*. The moxidectin resistant worms show side resistance to ivermectin and the ivermectin resistance is also overcome with the use of a mild MDR-reversing agent.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions which are both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

A further understanding of the invention may be obtained from the following non-limiting examples.

EXAMPLE 1

PCR Synthesis and Cloning of a 432 by DNA for a P-Glycoprotein Homolog from a cDNA Library of *H. contortus*

Based on the highly conserved ATP binding domains of *C. elegans* Pgp, a pair of degenerate PCR primers is designed. The sense primer is 5'-ACNGTNGCNYTNGTNGG-3' (which corresponds to SEQ ID NO:11) and the antisense primer is 5'-GCNSWNGTNGCYTCRTC-3' (which corresponds to SEQ ID NO:12). PCR is carried out for 40 cycles at a denaturing temperature of 94° C. for 1 minute, an annealing temperature of 37° C. for 1 minute, and an extension temperature of 72° C. for 3 minutes using an *H. contortus* cDNA library (Geary et al., *Mol. Biochem. Parasitol.*, 50: 295-306, 1992) as template. A 432 bp product is purified by agarose gel electrophoresis and the purified product is used as template for a second round of PCR amplification with the same primers. An enriched 432 bp product is subsequently cloned into TA vector (Invitrogen) according to standard protocols. Plasmids with inserts are transformed into *Escherichia coli* and then plated on Ampicillin LB plates containing a chromogenic substrate, X-GAL® (5-bromo-4-chloro-3-indolyl-β-D-galactopyranoside, commercially available from Gibco BRL, Bethesda, Md.) (Sambrook et al., Molecular Cloning. A Laboratory Manual, 2nd Ed., Cold Spring Harbor Laboratory Press, 1989). Ten clones are identified as ATP binding domain sequences of P-glycoprotein.

EXAMPLE 2

Screening of the *H. contortus* cDNA Library

The 432 bp fragment is excised by EcoRI, labelled by random priming with [$^{32}$P]d-CTP and used as a probe to screen the cDNA library (Sambrook et al., 1989). Approximately one million clones are screened and nine putative clones are identified. The positive clones are digested with PvuII and three of them containing inserts in the predicted size are subsequently sequenced.

EXAMPLE 3

Parasite Strains

Two pairs of ivermectin susceptible and resistant strains of *H. contortus* are used. The first pair is an ivermectin resistant strain (MFR) developed at the Merck Research Laboratories, Rahway, N.J. (Rohrer et al., *J. Parasitol.* 80: 493-497, 1994) and the ivermectin susceptible parent strain (MFS) from which the resistant strain is selected over seventeen generations of ivermectin selection. The second pair is an ivermectin resistant strain (ACR) developed at American Cyanamid Company, Princeton, N.J. and the ivermectin susceptible parent strain (ACS) from which the resistant strain is selected over fourteen generations of ivermectin selection. Strain MFR is reported to be 10× resistant at the $ED_{95}$ compared with MFS, and ACR, after twelve generations of selection, is found to be 6.3× resistant at the $ED_{95}$ compared with ACS.

EXAMPLE 4

RNA Extraction and Northern Hybridization

Figure 3:
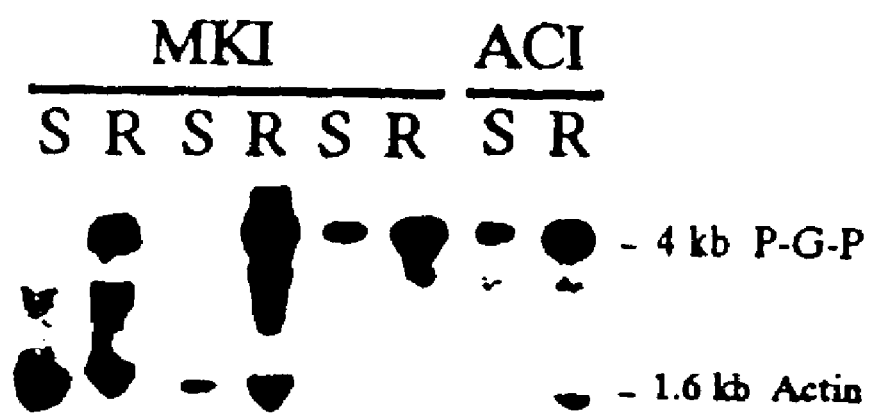
FIG. 3 shows the autoradiographs of the Northern blots of RNA extracted from eggs of ivermectin sensitive and resistant (MKIS and MKIR; ACIS and ACIR) nematode strains respectively. The [$^{32}$P]-432 bp PCR product, with homology to Pgp, is used as one probe and a [$^{32}$P]-actin fragment from pBA1 is used as a second probe.

Adult worms from ivermectin susceptible and resistant *H. contortus* are collected from the abomasum of sheep (Lubega and Prichard, *Biochem. Pharmacol.* 41: 93-101, 1991). Eggs from each strain are collected and isolated from faeces of sheep (Weston et al., *J. Parasitol.* 14: 159-164, 1984) which have been previously worm free and inoculated with one of the four *H. contortus* strains. Total RNA is extracted from tissues of the ivermectin susceptible and resistant strains, respectively, using TRIzoL® Reagent (Gibco BRL Life Technologies, Inc., Gaithersburg, Md., company protocol). Total RNA is run on denaturing formaldehyde agarose gel electrophoresis and transferred to H-bond nylon membranes. The membranes are prehybridized at 65° C. in 10% dextran disulfate, 1% SDS (sodium dodecylsulfate), 1.0M NaCl over 4 hours. The $^{32}$P-labelled 432 bp *H. contortus* Pgp fragment and an actin probe consisting of the 1.25 kb PstI fragment from pBA1 (Degen et al., *J. Biol. Chem.* 258: 12153, 1983) are mixed and incubated overnight with the membranes at 65° C. in the same hybridization buffer. The membranes are washed with 2×SSC (1:2 mixture of trisodium citrate and sodium chloride), 0.1% SDS at 65° C. for 30 minutes and 0.5×SSC at 35° C. for 1 hour and then autoradiographed. Image analyses of gel autoradiographs are made for quantitative determination of mRNA expression, using the IMAGE program (O'Neil et al., *Appl. Theor. Electrophor.*, 1: 163-167, 1989). Actin DNA probes from a mouse source, labelled and hybridized with the same blot, using the same method as above, is used as an internal control for mRNA loading. Results are shown in FIG. 3 (S=unselected strains; R=IVM selected strains; MKI=strains developed at Merck Research Laboratories, Rahway, N.J.; ACI=strains developed at American Cyanamid Company, Princeton, N.J.).

EXAMPLE 5

Southern Blots

Genomic DNA from both ivermectin susceptible and resistant strains is extracted (Sambrook et al., 1989). Four restriction enzymes EcoRI, ClaI, PvuII and PstI are used to digest the genomic DNA following the suppliers' directions. Each reaction is carried out with both ivermectin resistant and susceptible strains. After an overnight restriction enzyme digestion, samples are run on 1% agarose gels and then blotted onto H-bond membranes (Sambrook et al., 1989). The membranes with DNA are exposed under UV light to fix the DNA to the membranes. The membranes are prehybridized at 65° C. in buffer (10% sulfur dextran, 1% SDS and 1M NaCl) for at least 4 hours. The 432 bp fragment, labelled with [$^{32}$P], is added as a probe and hybridized with the genomic DNA in the prehybridization buffer, overnight. The membranes are subsequently washed twice with 2×SCC for 10 minutes, twice with 1×SCC for 15 minutes and then autoradiographed.

Results

PCR Amplification

Two rounds of PCR amplification generate a 432 bp product (FIG. 1) which is highly homologous to the conserved ATP binding domain of P-glycoprotein (FIG. 2A). The putative amino acid sequence (FIG. 2B) shows that this fragment is highly homologous to P-glycoprotein or multiple drug resistant proteins from *C. elegans*, mouse and other species. These data indicate that the 432 bp fragment represents the ATP binding sequence of an *H. contortus* Pgp homolog.

Expression of P-Glycoprotein mRNA in Ivermectin Resistant and Susceptible Strains of *H. contortus*

A single animal species may have different Pgp which may vary in size. Northern hybridization, with the 432 bp Pgp *H. contortus* homolog PCR product, shows that the molecular size of the mRNA for the *H. contortus* Pgp is about 4 kb. However, it is found that the mRNA levels of Pgp in ivermectin resistant and susceptible strains of *H. contortus* are different. For illustration, results of a number of representative Northern blots on *H. contortus* egg RNA are shown in FIG. 3.

The RNA is also probed with an actin probe to allow correction for different amounts of RNA loaded onto the gels. The intensity of the Pgp mRNA band varies with the strain of parasite. After correction for the intensity of the actin band, it is found that the amount of the 4 kb mRNA band recognized by the 432 bp Pgp probe is much higher in both ivermectin resistant strains compared with their respective ivermectin susceptible precursor strains. The increase varies from 250% to 670% after standardization for actin mRNA expression in drug resistant and susceptible strains (Table 1). Similar results are also obtained in comparisons of Pgp expression using RNA extracted from adult *H. contortus*.

Table 1 shows the relative intensity of mRNA for P-glycoprotein and actin in ivermectin susceptible and resistant *Haemonchus contortus* strains. RNA is extracted from eggs from the respective Merck (MKI) and American Cyanamid (ACI) paired strains. Each susceptible and resistant pair are processed at the same time. The RNA is separated on an agarose gel and probed with both *H. contortus* 432 bp Pgp and the actin pBA1 radiolabelled probes. The relative intensity of each band is determined, after gel autoradiography, by gel densitometry. The intensity of each Pgp band is corrected for intensity of its corresponding actin band in order to adjust for different amounts of RNA having been loaded onto the gels. All comparisons are made by pairs (resistant (R) versus corresponding susceptible (S)).

TABLE 1

| Strains comparison | Corrected R/S ratio |
|---|---|
| MKIS/MKIR | 6.77 |
| MKIS/MKIR | 6.08 |
| MKIS/MKIR | 2.57 |
| ACIS/ACIR | 4.19 |

Sequencing of P-Glycoprotein Homologs from the *H. contortus* cDNA Library

Longer clones (4.2 kb, 3.5 kb and 2.7 kb) identified using the 432 bp probe, which are shown to be homologous to P-glycoprotein, are fully or partially sequenced. FIGS. 4A to 4B show the full cDNA sequence for the PGP-A clone (4175 bp) which has high homology to known P-glycoprotein genes such as the Xenopus putative multidrug resistance protein (Xemdr) and the *C. elegans* cepgpA gene for P-glycoprotein A. FIGS. 5 and 6 show the partial sequence, in the sense direction (FIG. 5; PGP-A-5') and the antisense direction (FIG. 6; PGP-A-3') of the cDNA fragment which is also highly homologous to P-glycoprotein. FIGS. 7-9 illustrate, respectively, the putative amino acid translation of PGP-A cDNA, the partial cDNA sequence of the 3' end of the PGP-O clone (3.5 kb), antisense direction, and the partial cDNA sequence of 3' end of the PGP-B clone (2.7 kb), antisense direction.

Genomic DNA Differences Between Ivermectin Resistant and Susceptible Strains of *H. contortus* and Determination of a Nucleic Acid Probe for the Detection of Macrolactone Susceptibility or Resistance Genomic DNA hybridizations show that at least two bands are recognized by the 432 bp probe in ClaI and PstI digestion maps of both ivermectin susceptible and resistant strains. The EcoRI digestion maps show three strongly hybridizing bands and one light band for both susceptible and resistant strains. However, the PvuII digestion patterns are clearly different between the ivermectin resistant and susceptible strains (FIG. 10).

Figure 11:
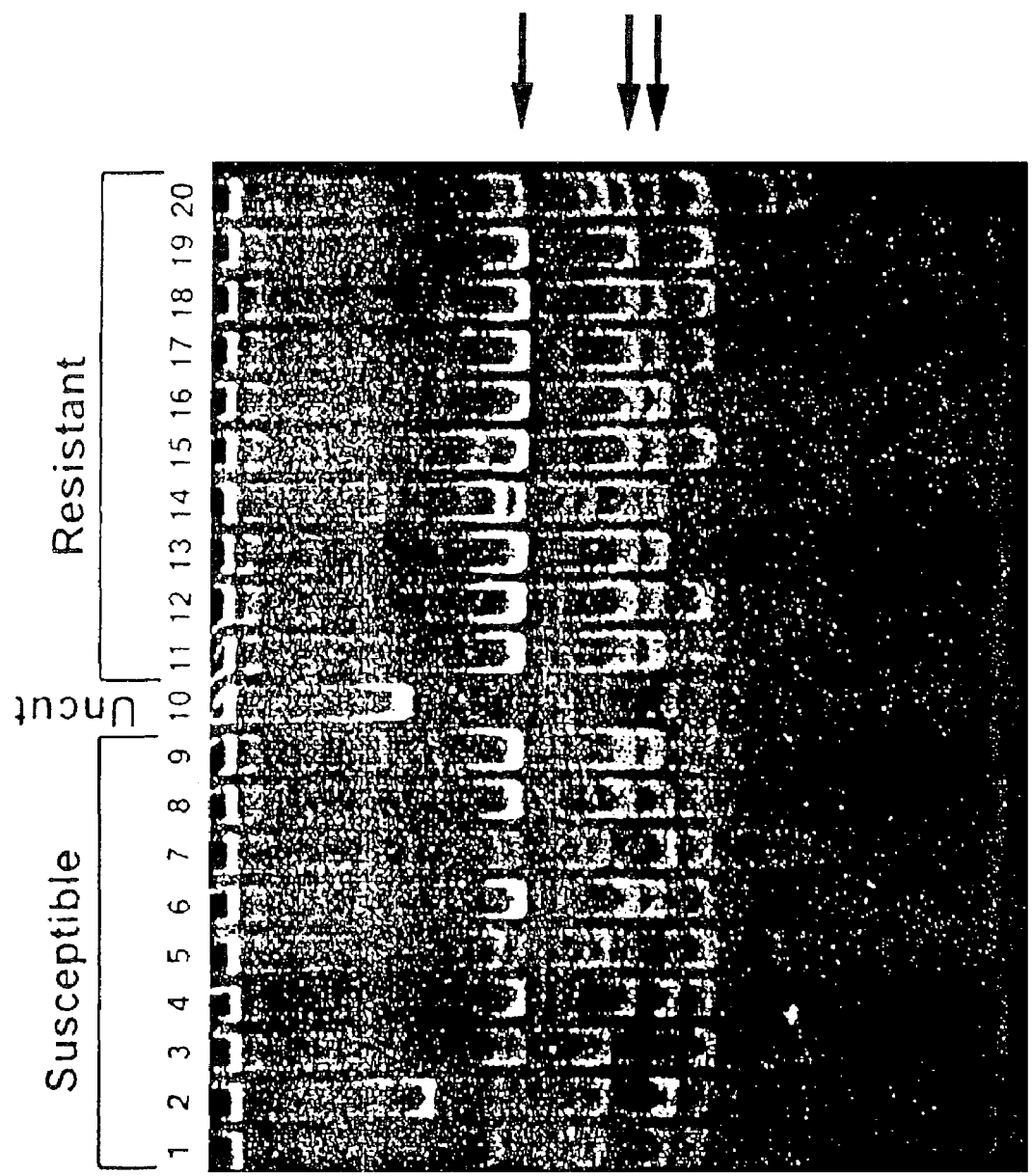
FIG. 11 shows the restriction length polymorphism of PCR products from the DNA of individual male adult worms from ivermectin susceptible (lanes 1-9) or resistant (lanes 11-20) *H. contortus* strains, generated with P-glycoprotein primers PGP2S and PGPAS followed by digestion with DdeI and separation on non-denaturing polyacrylamide gel electrophoresis. The arrows point to the three digestion fragments that are associated with resistance.
Figure 13A:
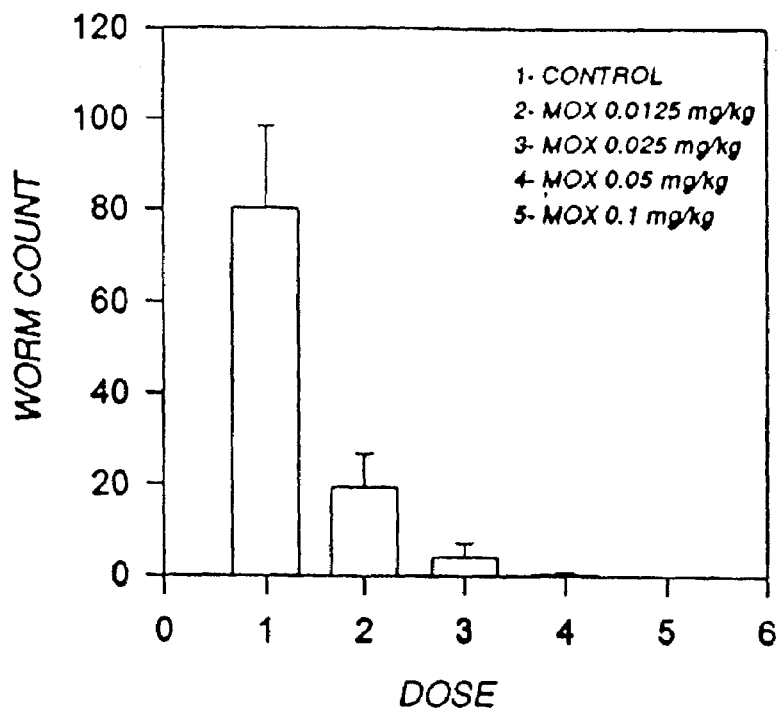
FIGS. 13A and 13B illustrate the efficacy of moxidectin (MOX) against *H. contortus* susceptible (FIG. 13A) or moxidectin-resistant (FIG. 13B) strains in jirds.
Figure 13B:
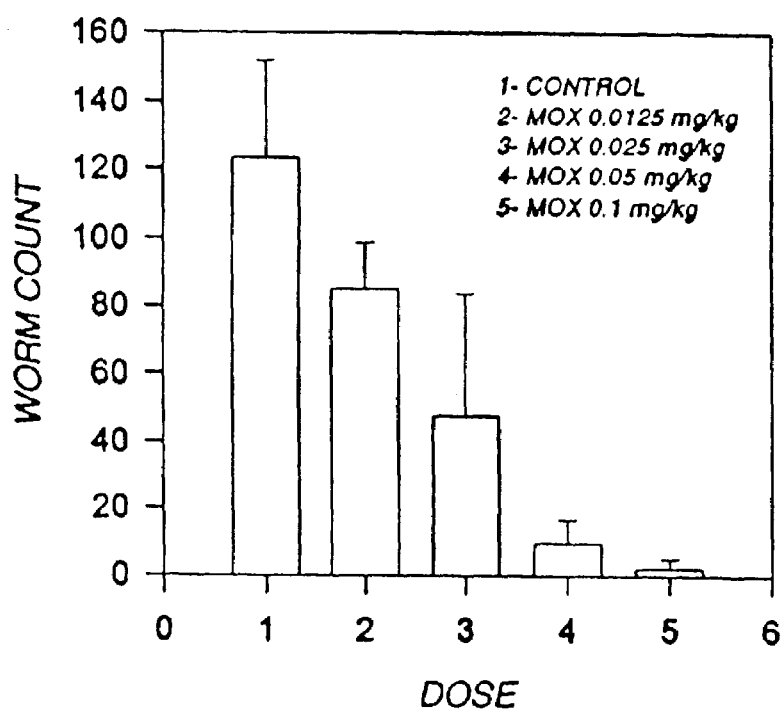
Figure 14A:
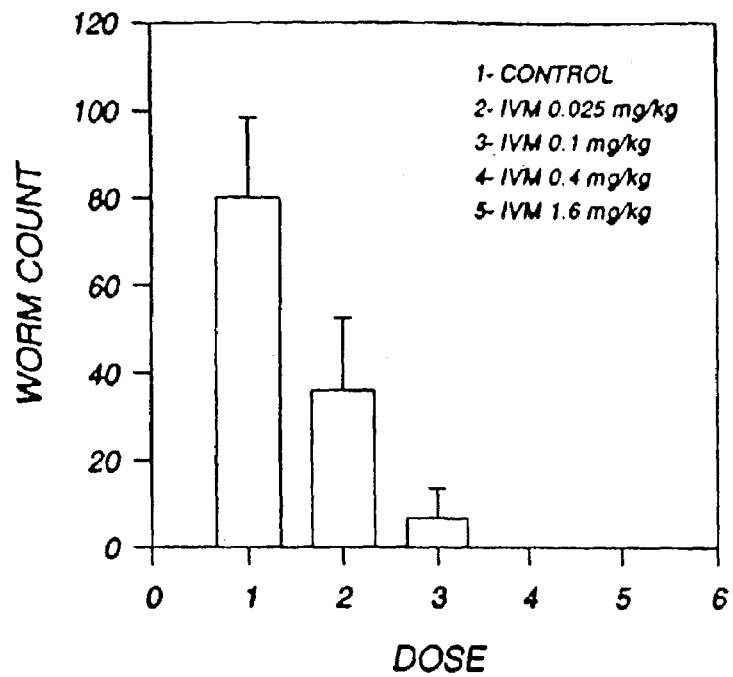
FIGS. 14A and 14B illustrate the efficacy of ivermectin (IVM) against *H. contortus* susceptible (FIG. 14A) and moxidectin-resistant (FIG. 14B) strains in jirds.
Figure 14B:
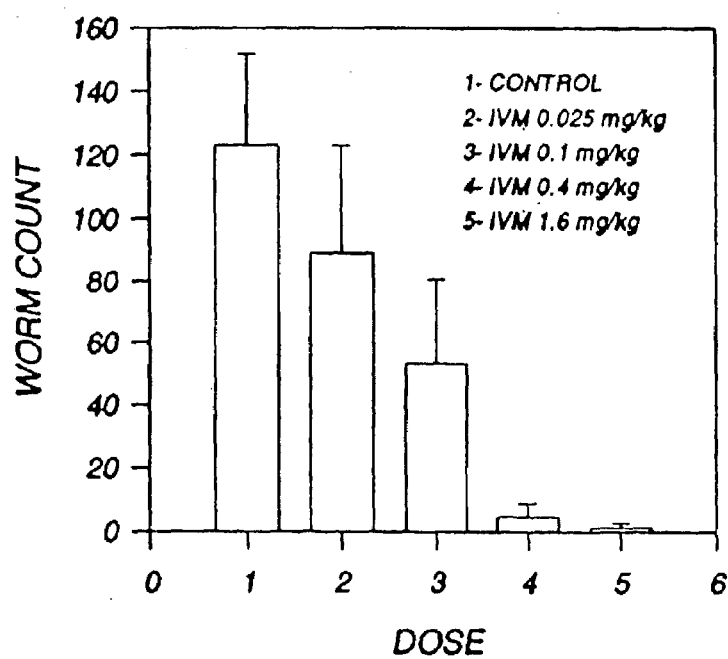

PCR products are generated using pairs of primers which are specific to parasite Pgp genes. In one example, the reverse primer is specific for a region 53 base pairs in length present in one of the Pgp clones (PGP-O). The forward primer anneals to a region common to multiple Pgp clones. Genomic DNA extracted from individual male *H. contortus* adults from IVM-sensitive (24 worms) and IVM-resistant (29 worms) populations (MKIS and MKIR) is used as template for amplification by PCR. The Pgp PCR products, approximately 900 bp in length, are digested with the restriction enzyme DdeI and the digestion products are separated by non-denaturing polyacrylamide gel electrophoresis (FIG. 11; see also FIGS. 17A-18C illustrating diagnostic restriction patterns for resistance after selection with either ivermectin or moxidectin, using different worm strains and different restriction enzymes). The digestion pattern for the worms from the susceptible population is variable, while that for the worms from the resistant population is more homogeneous. An identical digestion pattern of three bands (arrows) is found in 28 of the 29 worms from the resistant population (FIG. 11, lanes 11-18 and 20, for example), whereas only 4 or 5 worms from the susceptible population have this pattern (FIG. 11, lanes 6 and 9, for example). Examples of the probes are shown in FIGS. 12A and 12B.

These results are repeated several times. The PCR data and the Southern blot data clearly indicate that selection for macrocyclic lactone endectocide resistance causes a reduction in the genetic diversity of the Pgp alleles and that the differences in Pgp at the DNA level can be detected by specific probes techniques such as PCR (Polymerase Chain Reaction), Southern blot analysis and RFLP (Restriction Fragment Length Polymorphism).

Additional Methods

EXAMPLE 6

Establishing the $LD_{50}$ for Moxidectin and Ivermectin Against Moxidectin Susceptible and Resistant *H. contortus* in the Jird Jirds, which are fed on a standard commercial ration to which 0.02% hydrocortisone has been added 5 days prior to infection, are inoculated with 1000 exsheathed $L_3$ *H. contortus*. On day 10 after inoculation, the jirds are treated with either water or various doses of moxidectin or ivermectin orally. Each treatment group contains 6 jirds. The parasite strains and anthelmintic dose rates are shown in Table 2. The results of these dose titrations are shown in FIGS. 13A-14B. Probit analyses are used to estimate $LD_{50}$ levels for each anthelmintic against each strain. The estimated $LD_{50}$ of moxidectin against the susceptible and moxidectin resistant strains are 0.010 and 0.017 mg/kg, respectively, and for ivermectin the estimate $LD_{50}$ levels are 0.024 and 0.046 mg/kg, respectively.

The results indicate that (i) moxidectin is more potent than ivermectin against both the susceptible and moxidectin resistant strains, and (ii) moxidectin resistant *H. contortus* are side-resistant to ivermectin.

TABLE 2

DOSE RATES (mg/kg) OF MOXIDECTIN (MOX) OR IVERMECTIN (IVM) AGAINST *H. contortus* MOX-RESISTANT AND SUSCEPTIBLE STRAINS IN JIRDS (n = 6)

| COMPOUND (mg/kg) | SUSCEPTIBLE (PF14) | RESISTANT (MOF14) |
|---|---|---|
| CONTROL | — | — |
| MOX | 0.0125 | 0.0125 |
| MOX | 0.025 | 0.025 |
| MOX | 0.05 | 0.05 |
| MOX | 0.1 | 0.1 |
| IVM | 0.025 | 0.025 |
| IVM | 0.1 | 0.1 |
| IVM | 0.4 | 0.4 |
| IVM | 1.6 | 1.6 |

EXAMPLE 7

Determination of the Toxicity and the Efficacy of Verapamil Alone and in Combination With Ivermectin This experiment is performed to determine the toxicity of verapamil, a weak MDR-reversing agent, alone and in combination with ivermectin, the efficacy of verapamil alone against *H. contortus* and the effect of verapamil at 20 mg/kg on the efficacy of ivermectin against susceptible and moxidectin resistant worms. Dose rates of verapamil between 20 and 80 mg/kg are used alone or in combination with ivermectin at 0.024 and 0.046 mg/kg in jirds infected with susceptible or moxidectin resistant *H. contortus*. Verapamil is given concomitantly with ivermectin by the oral route. The results are shown in Table 3.

TABLE 3

DEMONSTRATION OF TOXICITY AND EFFICACY OF VERAPAMIL (VRP) WITH OR WITHOUT IVERMECTIN AGAINST *H. contortus* MOXIDECTIN RESISTANT OR SUSCEPTIBLE STRAINS IN JIRDS (n = # per group)

| COMPOUND (mg/kg) | # SUSCEPTIBLE (PF14) | # RESISTANT (MOF14) |
|---|---|---|
| CONTROL | 5 | 5 |
| VRP 20 | 5 | 5 |
| VRP 40 | 3 | 3 |
| VRP 60 | 3 | 3 |
| VRP 80 | 3 | 3 |
| IVM** | 5 | 5 |
| IVM/VRP 20 | 5 | 5 |
| IVM/VRP 40 | 5 | 5 |
| IVM/VRP 60 | 5 | 5 |
| IVM/VRP 80 | 5 | 5 |

**The dose of ivermectin is 0.024 mg/kg against strain PF14 and 0.046 mg/kg against strain MOF14.

As no deaths or other signs of toxicity are observed at a verapamil dose rate of 20 mg/kg, in the absence or presence of ivermectin, this dose rate is used for subsequent resistance reversing experiments. Verapamil alone is found to have no significant effect on worm counts at any of the dose rates used.

The toxicity of verapamil is summarized in Table 4.

TABLE 4

TOXICITY OF VERAPAMIL TO JIRDS

| VRP (mg/kg) | DEATHS - VRP ALONE | DEATHS - VRP + IVM* |
|---|---|---|
| 20 | 0/10 | 0/10 |
| 40 | 0/5 | 2/10 |
| 60 | 1/6 | 1/10 |
| 80 | 3/7 | 2/10 |

*Ivermectin is used at 0.24 mg/kg or 0.046 mg/kg according to Table 3.

Figure 15A:
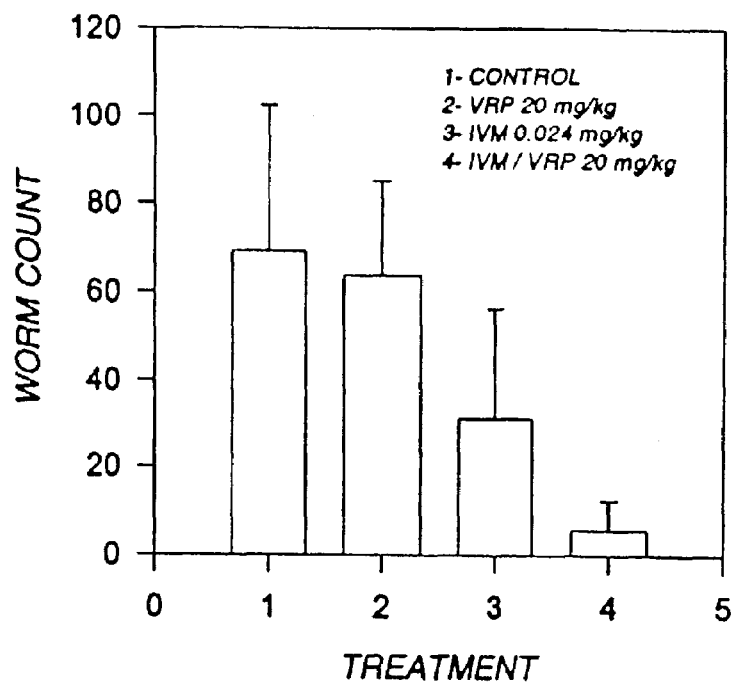
FIGS. 15A and 15B illustrate the efficacy of verapamil (VRP) with or without ivermectin (IVM; LD$_{50}$) against *H. contortus* susceptible (FIG. 15A) or moxidectin-resistant (FIG. 15B) strains in jirds.
Figure 15B:
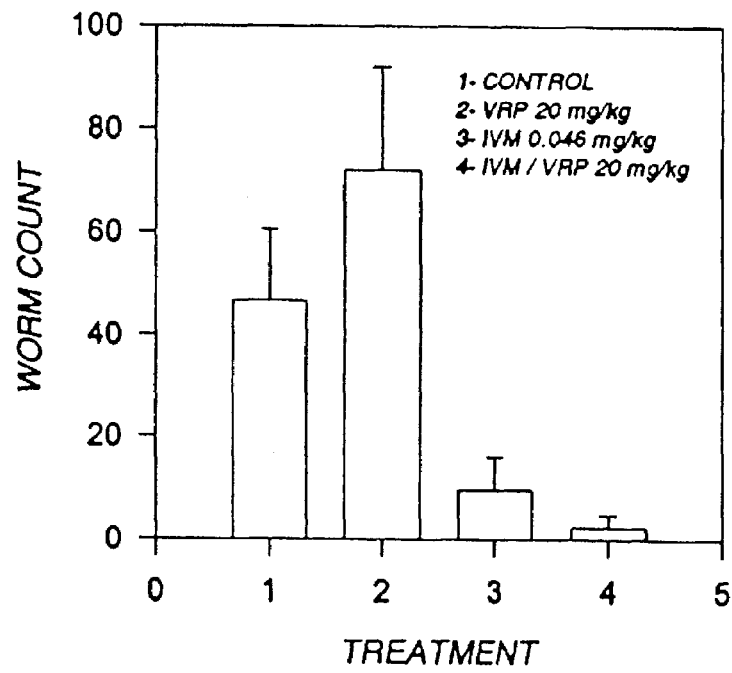

Because of the toxicity of verapamil at dose rates of 40 mg/kg and above, only the effects of verapamil at 20 mg/kg on the efficacy of ivermectin against susceptible and moxidectin resistant worms are considered. These results, shown in FIGS. 15A and 15B, are summarized in Table 5. Verapamil at 20 mg/kg significantly enhances the efficacy of ivermectin against the moxidectin resistant worms.

TABLE 5

EFFECT OF VERAPAMIL (20 mg/kg) ON THE EFFICACY (%) OF IVERMECTIN

| | STRAIN | |
|---|---|---|
| | SUSCEPTIBLE (PF14) | MOX-RESISTANT (MOF14) |
| TREATMENT (mg/kg) | % EFFICACY* | % EFFICACY* |
| CONTROL | 0 | 0 |
| VRP 20 | 17 (n.s.) | −53 (n.s.) |
| IVM# | 54 (A) | 79 (A) |
| IVM#/VRP 20 | 92 (A) | 96 (B) |

Ivermectin is administered at 0.024 mg/kg to jirds infected with PF14 strain and at 0.046 mg/kg to jirds infected with the MOF14 strain.
"n.s." indicates that the worm counts are not significantly different from the controls;
"A" means significantly different from the controls, but not from other worm counts, of the same strain, with the same letter;
"B" means significantly different worm counts from "A" for the same strain and dose rate of ivermectin.

EXAMPLE 8

The Effects of Verapamil on the Efficacy of Moxidectin and Ivermectin Against Susceptible and Moxidectin Resistant *H. contortus*

Figure 16A:
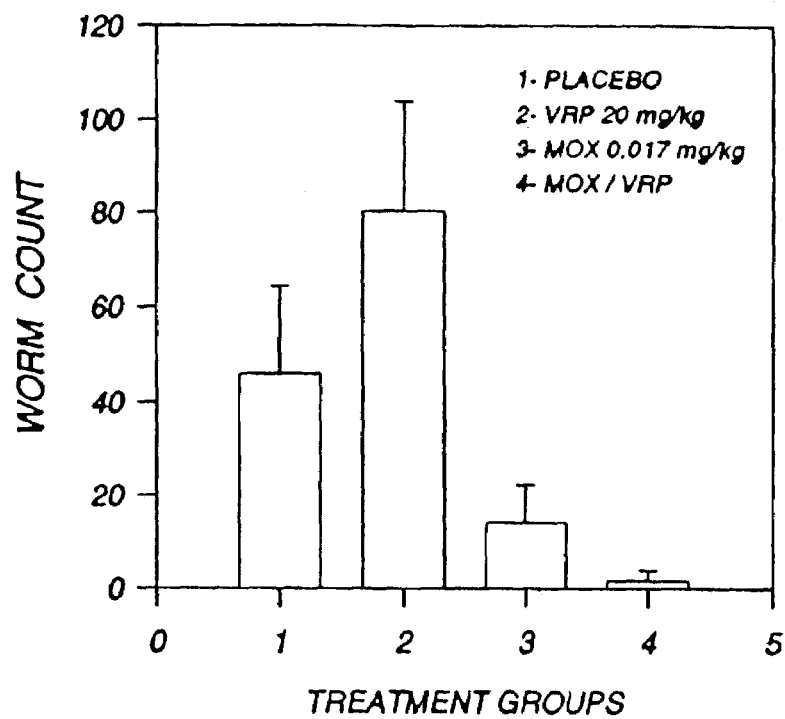
FIGS. 16A and 16B illustrate the efficacy of the combination of moxidectin (MOX.
Figure 16B:
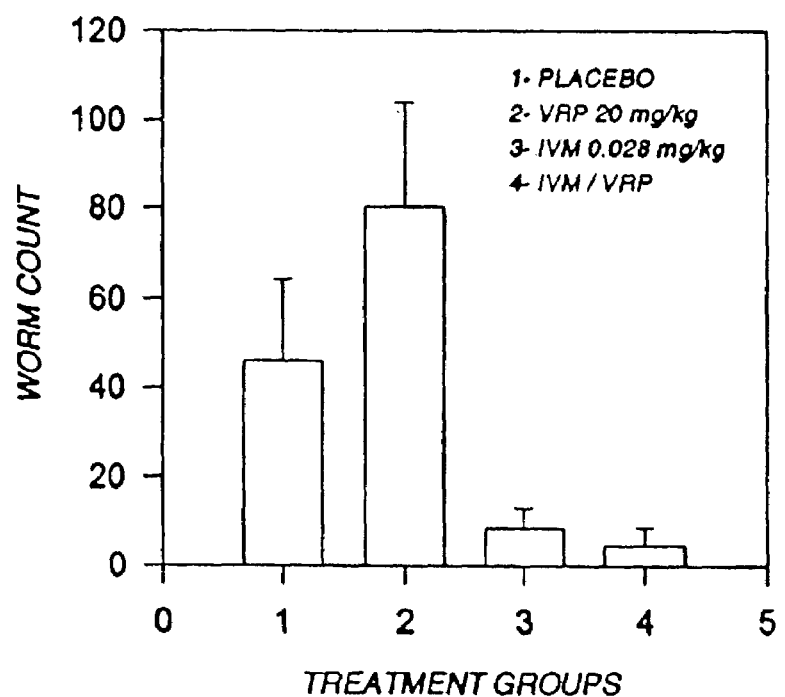
Figure 17A:
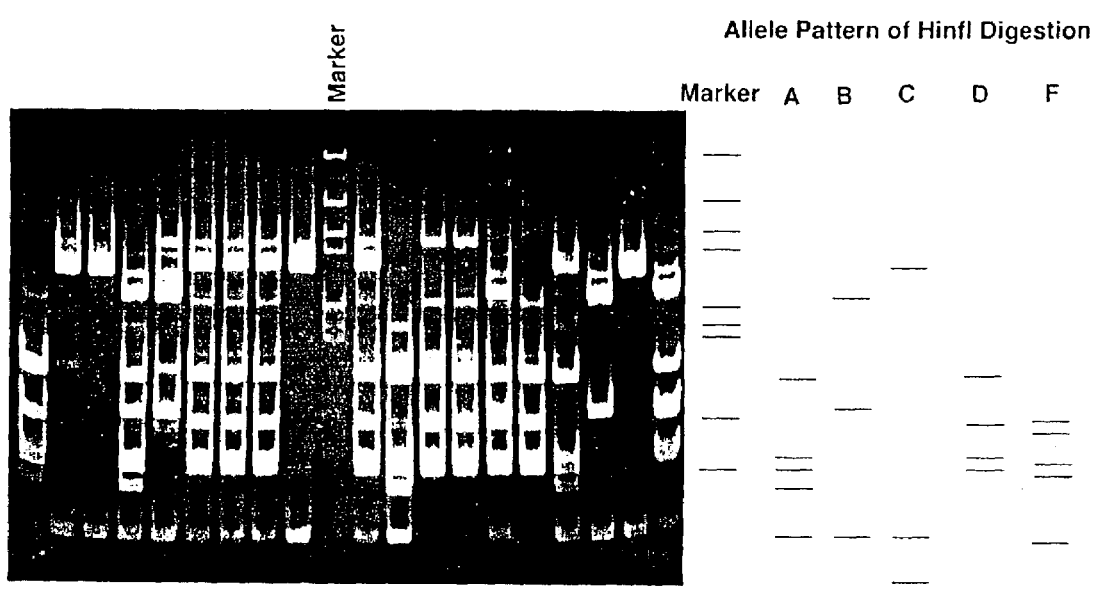
FIGS. 17A, 17B and 17C illustrate, respectively, the HinfI digestion of P-glycoprotein PCR fragments from the DNA of individual worms of susceptible, ivermectin-resistant and moxidectin-resistant *H. contortus*, using primers PGP2S and PGPAS, followed by digestion and separation on non-denaturing polyacrylamide gel electrophoresis. The arrows on the right side of FIGS. 17B and 17C point to the digestion fragments that are associated with resistance while the arrows on the left side point to the position and size of the standard markers.
Figure 17B:
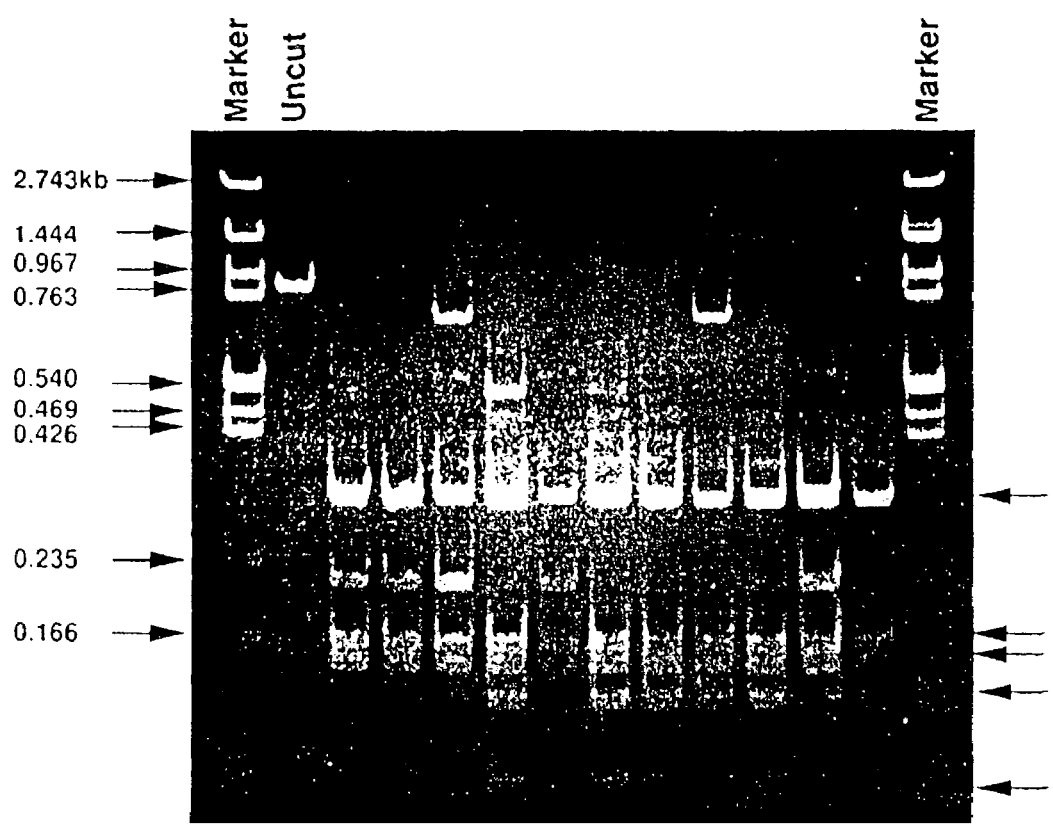
Figure 17C:
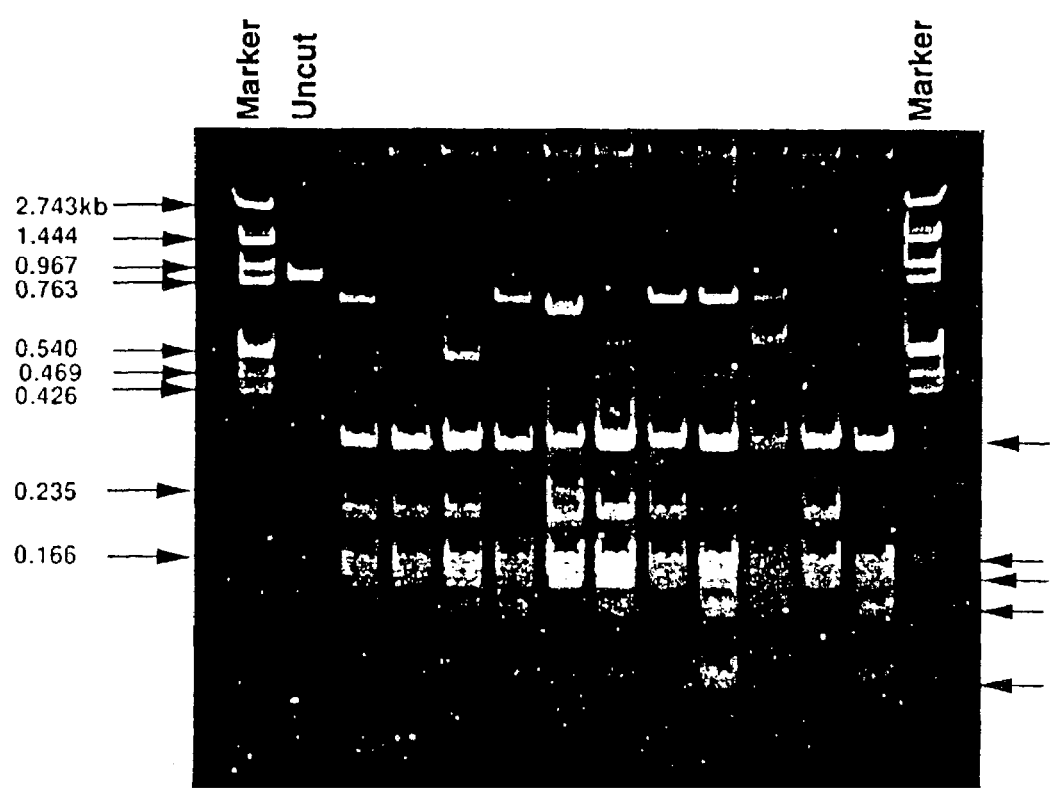
Figure 18A:
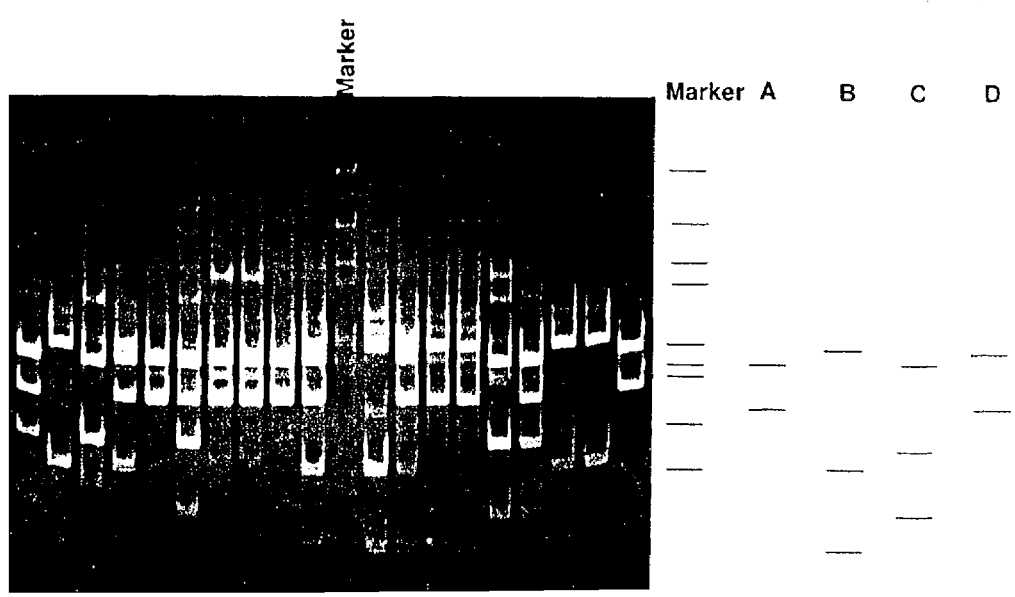
FIGS. 18A, 18B and 18C illustrate, respectively, the AluI digestion of P-glycoprotein PCR fragments from the DNA of individual worms of susceptible, ivermectin-resistant and moxidectin-resistant *H. contortus*, using primers PGP2S and PGPAS, followed by digestion and separation on non-denaturing polyacrylamide gel electrophoresis. The arrows on the right side of FIGS. 18B and 18C point to the digestion fragments that are associated with resistance while the arrows on the left side point to the position and size of the standard markers.
Figure 18B:
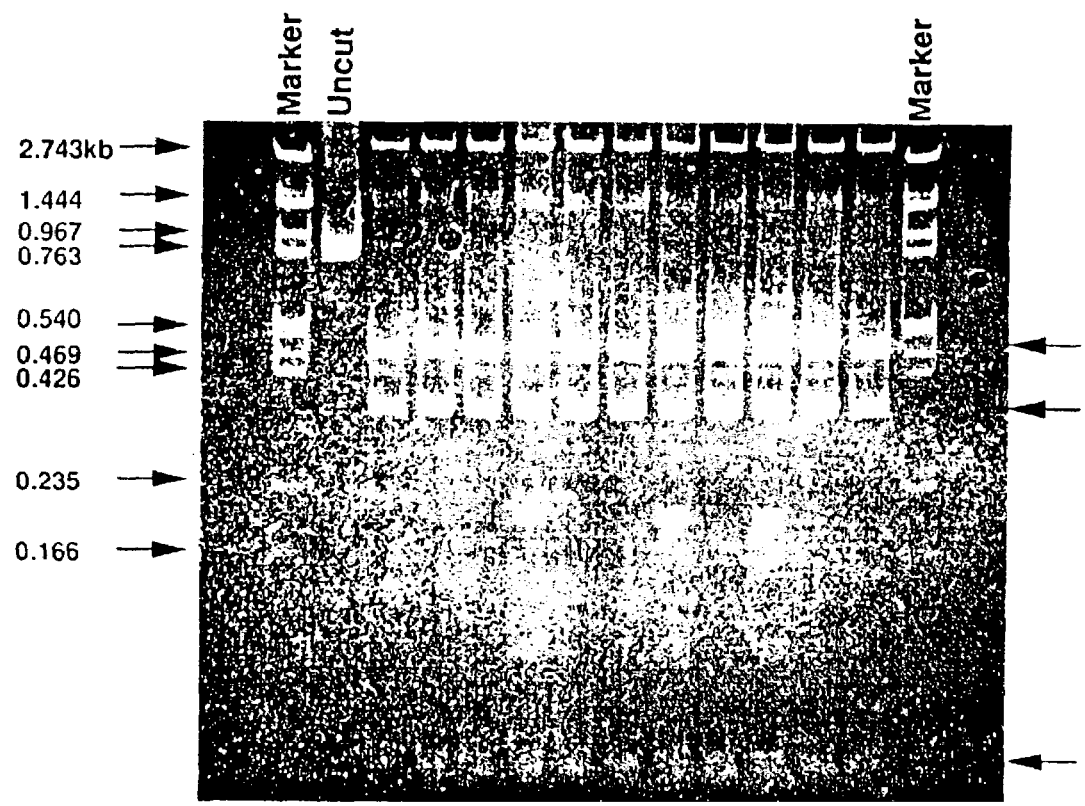
Figure 18C:
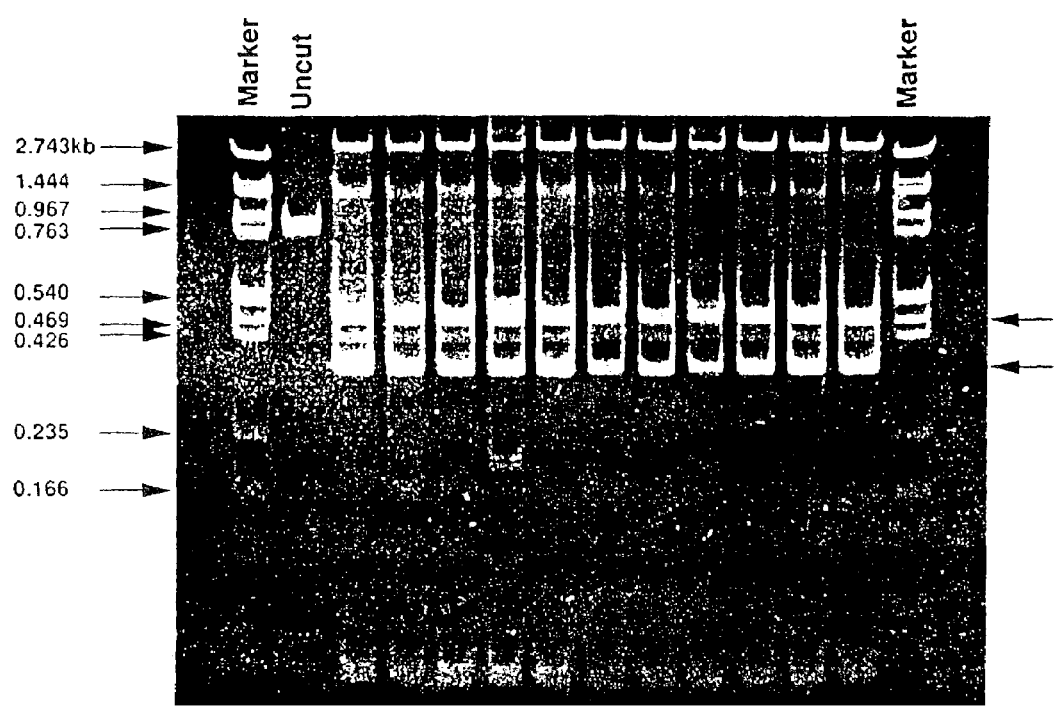

This experiment is performed on jirds to determine the effects of verapamil at 20 mg/kg on the efficacy of moxidectin and ivermectin against susceptible and moxidectin resistant *H. contortus*. All treatments have 7 jirds/group. The dose rates of moxidectin and ivermectin are selected to give approximately 50% efficacy in the absence of verapamil. Verapamil at 20 mg/kg significantly increases the efficacy of moxidectin against the resistant worms. The increase observed when verapamil is coadministered with ivermectin is not significant in this experiment as the efficacy obtained with ivermectin alone is already relatively high. The results are shown in Table 6 (see graphic representation of results in FIGS. 16A and 16B).

TABLE 6

EFFECT OF VERAPAMIL ON THE EFFICACY (%) OF MOXIDECTIN AND IVERMECTIN AGAINST THE MOXIDECTIN-RESISTANT STRAIN OF *H. contortus* (MOF14)

| TREATMENT | WORM COUNTS (MEAN ± S.E.) | EFFICACY (%) | SIGNIFICANCE AT $P < 0.05$ |
|---|---|---|---|
| PLACEBO | 46 ± 7 | — | A# |
| VRP* | 80 ± 9 | −73 | A |
| MOX (0.017 mg/kg) | 14 ± 3 | 70 | B |
| MOX (0.017 mg/kg) + VRP* | 2 ± 1 | 96 | C |
| IVM (0.028 mg/kg) | 9 ± 1 | 80 | B |
| IVM (0.028 mg/kg) + VRP* | 3 ± 1 | 93 | B |

*Verapamil is administered at 20 mg/kg. All treatments are by the oral route.
Different letters indicate the mean worm counts are statistically different. However, the ivermectin (± verapamil) results are not compared with the moxidectin (± verapamil) results. Verapamil by itself increases worm counts, but the mean count is not statistically different from the control.

This experiment confirms that the weak MDR-reversing agent verapamil overcomes resistance in nematodes to the macrolactones. These results are fully consistent with the above molecular evidence that macrolactone resistance is associated with the overexpression of P-glycoprotein homolog due to a change in P-glycoprotein DNA in resistant parasites. More potent MDR-reversing agents, such as cyclosporin A, SDZ-PSC 833 or other potent reversing agents can, at low dose rates, markedly increase the efficacy of macrocyclic lactone endectocides against resistant parasites.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

We claim:

1. A method for detecting the presence of P-glycoprotein A (PGP-A), P-glycoprotein B (PGP-B), or P-glycoprotein O (PGP-O) in *Haemonchus contortus*, which comprises the steps of:
   (a) preparing an antibody which is specific for a P-glycoprotein encoded by a nucleic acid molecule which comprises the nucleotide sequence of SEQ ID NO:3, SEQ ID NO:5, SEQ ID NO:7, or SEQ ID NO:8;
   (b) preparing a specimen of *Haemonchus contortus* for reaction with the antibody;
   (c) contacting the specimen with the antibody under suitable conditions that allow antibody-antigen binding to occur; and
   (d) determining the presence or absence of antibody-antigen binding, wherein detection of said binding is indicative of the presence of the P-glycoprotein in the specimen.

2. The method according to claim 1, wherein the nucleic acid molecule comprises the nucleotide sequence of SEQ ID NO:3.

3. The method according to claim 2, wherein the nucleotide sequence of SEQ ID NO:3 encodes the P-glycoprotein of SEQ ID NO:6.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 432 base pairs
      (B) TYPE: nucleic acid
      (C) STRANDEDNESS: double
      (D) TOPOLOGY: linear (ii) MOLECULE TYPE: cDNA (xi) SEQUENCE DESCRIPTION: SEQ ID NO: 1:

```
ACGGTGGCGT TTGTTGGGCA GTCTGGTTGT GGAAAAAGCA CTGTGAAGGC GTTGTTGGAC      60

GGTTTTACAA TCAAAACAAG GGCGTGATTA CGGACGCCGA AACATCAGA AACATGAACA      120

TACGCAATCT TCGTGAGCAA GTGTGTATTG TAAGCCAGGA ACCAACGCTG TTCGACTGTA     180

CCATCATGGA AACATCTGT TACGGTCTCG ATCGACCCCA AGCTCCTACG AACAGGTTGT      240

TGCTGCAGCA AAATCGGTCG AGTCGAAATG GCGAACATTC ACAATTTTGT GCTGGGACTA     300

CCAGAGGGTT ACGATACGCG TGTTGGTGAG AAAGGCACTC AGCTGTCAGG CGGACAGAAG     360

AAACGAATAG CCATAGCCAG AGCGCTGATT CGAGATCCGC CTATACTTCT GCTGGATGAG     420

GCTACGACGG CC                                                         432
```

(2) INFORMATION FOR SEQ ID NO: 2:

(i) SEQUENCE CHARACTERISTICS:
      (A) LENGTH: 144 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 2:

```
Thr Val Ala Phe Val Gly Gln Ser Gly Cys Gly Lys Ser Thr Val Lys
1               5                   10                  15

Ala Leu Leu Glu Arg Phe Tyr Asn Gln Asn Lys Gly Val Ile Thr Asp
            20                  25                  30

Ala Glu Asn Ile Arg Asn Met Asn Ile Arg Asn Leu Arg Glu Gln Val
        35                  40                  45

Cys Ile Val Ser Gln Glu Pro Thr Leu Phe Asp Cys Thr Ile Met Glu
    50                  55                  60

Asn Ile Cys Tyr Gly Leu Asp Asp Pro Lys Leu Leu Arg Thr Gly Cys
65                  70                  75                  80
```

```
Cys Cys Ser Lys Ile Gly Arg Val Glu Met Ala Asn Ile His Asn Phe
             85                  90                  95

Val Leu Gly Leu Pro Glu Gly Tyr Asp Thr Arg Val Gly Glu Lys Gly
            100                 105                 110

Thr Gln Leu Ser Gly Gly Gln Lys Lys Arg Ile Ala Ile Ala Arg Ala
            115                 120                 125

Leu Ile Arg Asp Pro Pro Ile Leu Leu Leu Asp Glu Ala Thr Thr Ala
    130                 135                 140
```

(2) INFORMATION FOR SEQ ID NO: 3:

(i) SEQUENCE CHARACTERISTICS:
        (A) LENGTH: 4175 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 3:

```
GGTTTAATTA CCCAAGTTTG AGAGATCGTT CTCAAGCTGG TAAAATGTTC GAAAAAGGCC      60
AAGATGATGA ACGTATACCA TTACTCGGTT CATCCAAGAA AAGTTCAATC GGCGAAGTCA     120
GTAAAAAAGA AGAACCGCCT ACAATAACAA ACCGTGGAAT TCTCTCCTTA GCCACTACAT     180
TGGATTATGT GCTTCTTGCG GCTGGTACGC TGGCGCCGTG TGTTCATGGC GCTGGATTCT     240
CAGTACTCGG TATTGTACTC GGTGGTATGA CGACAGTCTT TCTCAGAGCT CAGAACTCAG     300
AATTCGTTCT GGGCACTGTT AGTCGGGATC CTGAAGGGCT ACCAGCTCTT ACTAAGGAAG     360
AATTTGACAC ACTAGTACGT AGGTATTGCT TATACTACCT TGGATTAGGC TTTGCTATGT     420
TTGCAACATC TTATATACAG ATTGTGTGTT GGGAGACGTT CGCCGAACGA ATTACCCATA     480
AATTACGAAA AATTTATCTA AAAGCCATAC TTCGGCAGCA GATCTCATGG TTTGACATTC     540
AACAAACAGG AAATCTCACA GCTCGTCTAA CCGATGATCT CGAACGTGTT CGTGAAGGAC     600
TTGGTGATAA ACTGTCGCTT TTTATACAAA TGGTGTCTGC TTTTGTGGCT GGTTTCTGTG     660
TAGGATTCGC GTATAGCTGG TCAATGACGC TCGTGATGAT GGTCGTGGCG CCGTTTATAG     720
TTATTTCTGC TAATTGGATG TCAAAAATCG TTGCTACTAG GACCCAAGTT GAACAGGAAA     780
CCTACGCTGT TGCCGGTGCT ATAGCGGAGG AGACTTTCTC ATCGATACGA ACCGTACACT     840
CGATATGTGG CCATAAAAGA GAGCTAACAA GATTTGAGGC AGCGTTGGAG AAAGGACGTC     900
AGACAGGCCT TGTCAAATAT TTCTATATGG GTGTTGGTGT GGGATTTGGT CAGATGTGTA     960
CCTATGTGTC CTACGCCTTG GCTTTTTGGT ATGGCAGTGT ACTGATCATC AACGACCCTG    1020
CATTGGATCG TGGCCGAATT TTCACAGTCT TTTTTGCTGT GATGTCCGGC TCAGCAGCTC    1080
TCGGCACATG TCTGCCACAT CTTAACACCA TATCCATCGC TCGAGGAGCG GTACGAAGTG    1140
TACTGTCAGT GATTAATAGT CGTCCAAAAA TCGATCCCTA TTCGTTAGAT GGCATTGTGC    1200
TCAACAATAT GAGAGGATCT ATCCGCTTCA AGAACGTGCA TTTCTCCTAT CCTTCCCGAA    1260
GAACATTGCA GATATTGAAA GGTGTGTCAC TGCAAGTGTC GGCTGGCCAA AAAATTGCTT    1320
TGGTGGGTTC AAGCGGTTGT GGAAAGTCAA CGAACGTCAA TTTATTATTG AGATTTTATG    1380
ATCCGACAAG GGGAAAGGTA ACCATAGATG ATATTGATGT GTGTGATCTC AACGTGCAAA    1440
AACTTCGTGA ACAAATCGGT GTTGTTAGTC AGGAACCAGT GCTTTTCGAT GGCACACTAT    1500
TCGAAAATAT CAAGATGGGT TATGAACAGG CCACAATGGA GGAGGTCCAA GAAGCGTGCC    1560
GTGTGGCGAA TGCTGCCGAC TTCACCAAAC GACTTCCAGA AGGTTACGGC ACCCGAGTTG    1620
```

```
GTGAACGTGG TGTGCAGTTA AGTGGCGGAC AAAAGCAGCG AATTGCCATA GCTCGTGCGA    1680

TCATCAAGAA CCCTCGCATA CTGCTGCTCG ATGAAGCCAC CAGTGCTCTA GACACAGAAG    1740

CGGAATCAAT CGTGCAAGAG GCTCTGGAGA AGGCTCAAAA AGGGAGAACA ACCGTCATTG    1800

TAGCGCATCG TCTGTCTACT ATCAGAAACG TGGATCAGAT TTTCGTTTTC AAGAACGGAA    1860

CGATCGTTGA GCAGGGCACT CATGCCGAGT TGATGAACAA ACGTGGAGTA TTCTTTGAAA    1920

TGACTCAAGC ACAAGTCCTC CGACAAGAGA AGGAAGAGGA AGTTTTAGAT AGCGATGCGG    1980

AATCCGATGT CGTGTCACCG GATATTGCAT TACCCCATCT TAGTTCACTT CGATCCCGTA    2040

AAGAATCCAC AAGAAGTGCT ATCTCCGCGG TCCCCAGCGT TCGAAGTATG CAAATCGAAA    2100

TGGAGGACCT TCGTGCCAAA CCAACTCCAA TGTCGAAAAT TTTCTATTTT AACCGTGACA    2160

AATGGGATA TTTCATTTTG GGACTCATCG CCTGTATTAT TACTGAACT GTTACACCGA     2220

CATTTGCAGT TTTATATGCG CAGATCATAC AGGTATACTC GGAACCTGTT GATCAAATGA    2280

AAGGCCATGT GCTGTTCTGG TGTGGAGCTT TCATCGTCAT TGGTCTCGTA CACGCTTTTG    2340

CGTTCTTTTT CTCGGCTATT TGTTTGGGAC GTTGCGGCGA AGCGTTAACG AAAAAATTAC    2400

GTTTCGAGGC GTTCAAGAAC CTTCTGCGAC AGAATGTGGG ATTCTACGAC GATATCCGAC    2460

ACGGTACCGG TAAACTCTGT ACGCGATTTG CTACAGATGC ACCCAATGTC CGATATGTGT    2520

TCACTCGACT TCCGGGTGTG CTTTCATCGG TGGTGACCAT AATTGGAGCT TTGGTTATTG    2580

GATTCATCTT CGGGTGGCAG CTGGCTTTGA TTCTTATGGT GATGGTACCG TTGATCATCG    2640

GTAGTGGATA CTTCGAGATG CGCATGCAGT TTGGTAAGAA GATGCGTGAC ACAGAGCTTC    2700

TTGAAGAGGC TGGGAAAGTT GCCTCTCAAG CCGTGGAGAA CATTCGTACC GTGCATGCCC    2760

TGAATAGGCA AGAGCAGTTC CATTTCATGT ATTGCGAGTA TTTGAAGGAA CCCTATCGAG    2820

AAAATCTTTG CCAGGCGCAC ACCTACGGGG GTGTATTCGC GTTCTCACAA TCGTTGTTAT    2880

TCTTTATGTA TGCTGTAGCA TTTTGGATTG GTGCAATCTT CGTGGACAAC CACAGCATGC    2940

AACCGATTGA CGTTTACCGA GTATTTTTCG CGTTCATGTT TTGTGGACAA ATGGTCGGCA    3000

ACATTTCTTC TTTTATTCCT GACGTTGTGA AAGCTCGCCT GGCTGCATCG CTCCTTTTCT    3060

ACCTTATCGA ACACCCATCA GAAATTGATA ATTTGTCCGA GGATGGTGTC ACGAAGAAAA    3120

TCTCTGGTCA TATCTCGTTC CGCAATGTCT ATTTCAATTA TCCGACAAGA AGACAGATCA    3180

GAGTACTCCG TGGACTTAAC CTAGAGATAA ATCCTGGCAC GACGGTAGCG CTTGTTGGGC    3240

AGTCTGGTTG TGGAAAAAGC ACTGTGATGG CGTTGTTGGA ACGGTTTTAC AATCAAAACA    3300

AGGGCGTGAT TACGGTGGAC GGCGAAAACA TCAGAAACAT GAACATACGC AATCTTCGTG    3360

AGCAAGTGTG TATTGTTAGC CAGGAACCAA CGCTGTTCGA CTGTACCATC ATGGAAAACA    3420

TCTGTTACGG TCTCGATGAC CCCAAGCCGT CCTACGAACA GGTTGTTGCT GCAGCAAAAA    3480

TGGCGAACAT TCACAATTTT GTGCTGGGAC TACCAGAGGG TTACGATACG CGTGTTGGTG    3540

ARAAAGGCAC TCAGCTGTCA GGCGGACAGA AGCAACGAAT AGCCATAGCC AGAGCGCTGA    3600

TTCGAGATCC GCCTATACTT CTGCTGGATG AGGCGACAAG CGCGCTGGAT ACCGAGAGTG    3660

AAAAGATCGT GCAAGACGCC CTAGAGGTTG CTCGCCAAGG TAGAACGTGC CTTGTAATTG    3720

CCCATCGCCT TTCTACAATT CAAGACAGTG ACGTCATAGT GATGATCCAG GAGGGGAAAG    3780

CTACAGACAG AGGCACTCAT GAACATTTAC TGATGAAGAA CGATCTATAC AAACGGCTAT    3840

GCGAAACACA ACGACTCGTT GAATCACAAT GAGTTTTTAG TGCCAATCGA TAGTGATCGA    3900

TAAGCTATGG ATTAGTCTTT AACACTTACT GATCATATGA CTCTATCTCG TGCTTTATTA    3960

TAATGTACAT ATGTAATGGT TTTGATCTTA CATATCTTGT AATTGGTCCT CACTATCATA    4020
```

```
ATGCCTTTAG TAGTATATTA ACAGTTTTAT TAATACAACT TAAGTAACAT ATTAACAATT    4080

TTATTAATAT AACTTAAGTA AGATATTGAC AGTTTTATTA ATTTGGAGGA TTTATAATAA    4140

AACCTCGTGC CGCTCGTGCC GAAACGATAT CAAGC                               4175
```

(2) INFORMATION FOR SEQ ID NO: 4:

(i) SEQUENCE CHARACTERISTICS:
        (A) LENGTH: 1810 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 4:

```
GGTTTAATTA CCCAAGTTTG AGAGATCGTT CTCAAGCTGG TAAAATGTTC GAAAAGGCC       60

AAGATGATGA ACGTATACCA TTACTCGGTT CATCCAAGAA AAGTTCAATC GGCGAAGTCA    120

GTAAAAAGA AGAACCGCCT ACAATAACAA ACCGTGGAAT TCTCTCCTTA GCCACTACAT      180

TGGATTATGT GCTTCTTGCG GCTGGTACGC TGGCGCCGTG TGTTCATGGC GCTGGATTCT    240

CAGTACTCGG TATTGTACTC GGTGGTATGA CGACAGTCTT TCTCAGAGCT CAGAACTCAG    300

AATTCGTTCT GGGCACTGTT AGTCGGGATC CTGAAGGGCT ACCAGCTCTT ACTAAGGAAG    360

AATTTGACAC ACTAGTACGT AGGTATTGCT TATACTACCT TGGATTAGGC TTTGCTATGT    420

TTGCAACATC TTATATACAG ATTGTGTGTT GGGAGACGTT CGCCGAACGA ATTACCCATA    480

AATTACGAAA AATTTATCTA AAAGCCATAC TTCGGCAGCA GATCTCATGG TTTGACATTC    540

AACAAACAGG AAATCTCACA GCTCGTCTAA CCGATGATCT CGAACGTGTT CGTGAAGGAC    600

TTGGTGATAA ACTGTCGCTT TTTATACAAA TGGTGTCTGC TTTTGTGGCT GGTTTCTGTG    660

TAGGATTCGC GTATAGCTGG TCAATGACGC TCGTGATGAT GGTCGTGGCG CCGTTTATAG    720

TTATTTCTGC TAATTGGATG TCAAAAATCG TTGCTACTAG GACCCAAGTT GAACAGGAAA    780

CCTACGCTGT TGCCGGTGCT ATAGCGGAGG AGACTTTCTC ATCGATACGA ACCGTACACT    840

CGATATGTGG CCATAAAAGA GAGCTAACAA GATTTGAGGC AGCGTTGGAG AAAGGACGTC    900

AGACAGGCCT TGTCAAATAT TTCTATATGG GTGTTGGTGT GGGATTTGGT CAGATGTGTA    960

CCTATGTGTC CTACGCCTTG GCTTTTTGGT ATGGCAGTGT ACTGATCATC AACGACCCTG   1020

CATTGGATCG TGGCCGAATT TTCACAGTCT TTTTTGCTGT GATGTCCGGC TCAGCAGCTC   1080

TCGGCACATG TCTGCCACAT CTTAACACCA TATCCATCGC TCGAGGAGCG GTACGAAGTG   1140

TACTGTCAGT GATTAATAGT CGTCCAAAAA TCGATCCCTA TTCGTTAGAT GGCATTGTGC   1200

TCAACAATAT GAGAGGATCT ATCCGCTTCA AGAACGTGCA TTTCTCCTAT CCTTCCCGAA   1260

GAACATTGCA GATATTGAAA GGTGTGTCAC TGCAAGTGTC GGCTGGCCAA AAAATTGCTT   1320

TGGTGGGTTC AAGCGGTTGT GGAAAGTCAA CGAACGTCAA TTTATTATTG AGATTTTATG   1380

ATCCGACAAG GGGAAAGGTA ACCATAGATG ATATTGATGT GTGTGATCTC AACGTGCAAA   1440

AACTTCGTGA ACAAATCGGT GTTGTTAGTC AGGAACCAGT GCTTTTCGAT GGCACACTAT   1500

TCGAAAATAT CAAGATGGGT TATGAACAGG CCACAATGGA GGAGGTCCAA GAAGCGTGCC   1560

GTGTGGCGAA TGCTGCCGAC TTCACCAAAC GACTTCCAGA AGGTTACGGC ACCCGAGTTG   1620

GTGAACGTGG TGTGCAGTTA AGTGGCGGAC AAAAGCAGCG AATTGCCATA GCTCGTGCGA   1680

TCATCAAGAA CCCTCGCATA CTGCTGCTCG ATGAAGCCAC CAGTGCTCTA GACACAGAAG   1740

CGGAATCAAT CGTGCAAGAG GCTCTGGAGA AGGCTCAAAA AGGGAGAACA ACCGTCATTG   1800
```

TAGCGCATCG 1810

(2) INFORMATION FOR SEQ ID NO: 5:

(i) SEQUENCE CHARACTERISTICS:
        (A) LENGTH: 2698 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 5:

```
AGTGCTTTTC GATGGCACAC TATTCGAAAA TATCAAGATG GGTTATGAAC AGGCCACAAT      60
GGAGGAGGTC CAAGAAGCGT GCCGTGTGGC GAATGCTGCC GACTTCACCA AACGACTTCC     120
AGAAGGTTAC GGCACCCGAG TTGGTGAACG TGGTGTGCAG TTAAGTGGCG ACAAAAGCA      180
GCGAATTGCC ATAGCTCGTG CGATCATCAA GAACCCTCGC ATACTGCTGC TCGATGAAGC     240
CACCAGTGCT CTAGACACAG AAGCGGAATC AATCGTGCAA GAGGCTCTGG AGAAGGCTCA     300
AAAAGGGAGA CAACCGTCA TTGTAGCGCA TCGTCTGTCT ACTATCAGAA ACGTGGATCA      360
GATTTTCGTT TTCAAGAACG GAACGATCGT TGAGCAGGGC ACTCATGCCG AGTTGATGAA     420
CAAACGTGGA GTATTCTTTG AAATGACTCA AGCACAAGTC CTCCGACAAG AGAAGGAAGA     480
GGAAGTTTTA GATAGCGATG CGGAATCCGA TGTCGTGTCA CCGGATATTG CATTACCCCA     540
TCTTAGTTCA CTTCGATCCC GTAAAGAATC ACAAGAAGT GCTATCTCCG CGGTCCCCAG      600
CGTTCGAAGT ATGCAAATCG AAATGGAGGA CCTTCGTGCC AAACCAACTC AATGTCGAA      660
AATTTTCTAT TTTAACCGTG ACAAATGGGG ATATTTCATT TTGGGACTCA TCGCCTGTAT     720
TATTACTGGA ACTGTTACAC CGACATTTGC AGTTTTATAT GCGCAGATCA TACAGGTATA     780
CTCGGAACCT GTTGATCAAA TGAAAGGCCA TGTGCTGTTC TGGTGTGGAG CTTTCATCGT     840
CATTGGTCTC GTACACGCTT TTGCGTTCTT TTTCTCGGCT ATTTGTTTGG GACGTTGCGG     900
CGAAGCGTTA ACGAAAAAAT TACGTTTCGA GGCGTTCAAG AACCTTCTGC GACAGAATGT     960
GGGATTCTAC GACGATATCC GACACGGTAC CGGTAAACTC TGTACGCGAT TGCTACAGA    1020
TGCACCCAAT GTCCGATATG TGTTCACTCG ACTTCCGGGT GTGCTTTCAT CGGTGGTGAC    1080
CATAATTGGA GCTTTGGTTA TTGGATTCAT CTTCGGGTGG CAGCTGGCTT TGATTCTTAT    1140
GGTGATGGTA CCGTTGATCA TCGGTAGTGG ATACTTCGAG ATGCGCATGC AGTTTGGTAA    1200
GAAGATGCGT GACACAGAGC TTCTTGAAGA GGCTGGGAAA GTTGCCTCTC AAGCCGTGGA    1260
GAACATTCGT ACCGTGCATG CCCTGAATAG GCAAGAGCAG TTCCATTTCA TGTATTGCGA    1320
GTATTTGAAG GAACCCTATC GAGAAAATCT TTGCCAGGCG CACACCTACG GGGTGTATT     1380
CGCGTTCTCA CAATCGTTGT TATTCTTTAT GTATGCTGTA GCATTTTGGA TTGGTGCAAT    1440
CTTCGTGGAC AACCACAGCA TGCAACCGAT TGACGTTTAC CGAGTATTTT TCGCGTTCAT    1500
GTTTTGTGGA CAAATGGTCG GCAACATTTC TTCTTTTATT CCTGACGTTG TGAAAGCTCG    1560
CCTGGCTGCA TCGCTCCTTT TCTACCTTAT CGAACACCCA TCAGAAATTG ATAATTTGTC    1620
CGAGGATGGT GTCACGAAGA AAATCTCTGG TCATATCTCG TTCCGCAATG TCTATTTCAA    1680
TTATCCGACA AGAAGACAGA TCAGAGTACT CCGTGGACTT AACCTAGAGA TAAATCCTGG    1740
CACGACGGTA GCGCTTGTTG GGCAGTCTGG TTGTGGAAAA AGCACTGTGA TGGCGTTGTT    1800
GGAACGGTTT TACAATCAAA ACAAGGGCGT GATTACGGTG GACGGCGAAA ACATCAGAAA    1860
CATGAACATA CGCAATCTTC GTGAGCAAGT GTGTATTGTT AGCCAGGAAC CAACGCTGTT    1920
```

-continued

```
CGACTGTACC ATCATGGAAA ACATCTGTTA CGGTCTCGAT GACCCCAAGC CGTCCTACGA    1980

ACAGGTTGTT GCTGCAGCAA AAATGGCGAA CATTCACAAT TTTGTGCTGG GACTACCAGA    2040

GGGTTACGAT ACGCGTGTTG GTGARAAAGG CACTCAGCTG TCAGGCGGAC AGAAGCAMCG    2100

AATAGCCATA GCCAGAGCGC TGATTCGAGA TCCGCCTATA CTTCTGCTGG ATGAGGCGAC    2160

AAGCGCGCTG GATACCGAGA GTGAAAAGAT CGTGCAAGAC GCCCTAGAGG TTGCTCGCCA    2220

AGGTAGAACG TGCCTTGTAA TTGCCCATCG CCTTTCTACA ATTCAAGACA GTGACGTCAT    2280

AGTGATGATC CAGGAGGGGA AAGCTACAGA CAGAGGCACT CATGAACATT TACTGATGAA    2340

GAACGATCTA TACAAACGGC TATGCGAAAC ACAACGACTC GTTGAATCAC AATGAGTTTT    2400

TAGTGCCAAT CGATAGTGAT CGATAAGCTA TGGATTAGTC TTTAACACTT ACTGATCATA    2460

TGACTCTATC TCGTGCTTTA TTATAATGTA CATATGTAAT GGTTTTGATC TTACATATCT    2520

TGTAATTGGT CCTCACTATC ATAATGCCTT TAGTAGTATA TTAACAGTTT TATTAATACA    2580

ACTTAAGTAA CATATTAACA ATTTTATTAA TATAACTTAA GTAAGATATT GACAGTTTTA    2640

TTAATTTGGA GGATTTATAA TAAAACCTCG TGCCGCTCGT GCCGAAACGA TATCAAGC     2698
```

(2) INFORMATION FOR SEQ ID NO: 6:

(i) SEQUENCE CHARACTERISTICS:
        (A) LENGTH: 1275 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Met Phe Glu Lys Gly Gln Asp Asp Glu Arg Ile Pro Leu Leu Gly Ser
1               5                  10                  15

Ser Lys Lys Ser Ser Ile Gly Glu Val Ser Lys Glu Glu Pro Pro
            20                  25                  30

Thr Ile Thr Asn Arg Gly Ile Leu Ser Leu Ala Thr Thr Leu Asp Tyr
        35                  40                  45

Val Leu Leu Ala Ala Gly Thr Leu Ala Pro Cys Val His Gly Ala Gly
    50                  55                  60

Phe Ser Val Leu Gly Ile Val Leu Gly Gly Met Thr Thr Val Phe Leu
65                  70                  75                  80

Arg Ala Gln Asn Ser Glu Phe Val Leu Gly Thr Val Ser Arg Asp Pro
                85                  90                  95

Glu Gly Leu Pro Ala Leu Thr Lys Glu Glu Phe Asp Thr Leu Val Arg
            100                 105                 110

Arg Tyr Cys Leu Tyr Tyr Leu Gly Leu Gly Phe Ala Met Phe Ala Thr
        115                 120                 125

Ser Tyr Ile Gln Ile Val Cys Trp Glu Thr Phe Ala Glu Arg Ile Thr
    130                 135                 140

His Lys Leu Arg Lys Ile Tyr Leu Lys Ala Ile Leu Arg Gln Gln Ile
145                 150                 155                 160

Ser Trp Phe Asp Ile Gln Gln Thr Gly Asn Leu Thr Ala Arg Leu Thr
                165                 170                 175

Asp Asp Leu Glu Arg Val Arg Glu Gly Leu Gly Asp Lys Leu Ser Leu
            180                 185                 190

Phe Ile Gln Met Val Ser Ala Phe Val Ala Gly Phe Cys Val Gly Phe
        195                 200                 205
```

-continued

```
Ala Tyr Ser Trp Ser Met Thr Leu Val Met Met Val Ala Pro Phe
    210                 215                 220

Ile Val Ile Ser Ala Asn Trp Met Ser Lys Ile Val Ala Thr Arg Thr
225                 230                 235                 240

Gln Val Glu Gln Glu Thr Tyr Ala Val Ala Gly Ala Ile Ala Glu Glu
                245                 250                 255

Thr Phe Ser Ser Ile Arg Thr Val His Ser Ile Cys Gly His Lys Arg
            260                 265                 270

Glu Leu Thr Arg Phe Glu Ala Ala Leu Glu Lys Gly Arg Gln Thr Gly
        275                 280                 285

Leu Val Lys Tyr Phe Tyr Met Gly Val Gly Val Gly Phe Gly Gln Met
    290                 295                 300

Cys Thr Tyr Val Ser Tyr Ala Leu Ala Phe Trp Tyr Gly Ser Val Leu
305                 310                 315                 320

Ile Ile Asn Asp Pro Ala Leu Asp Arg Gly Arg Ile Phe Thr Val Phe
                325                 330                 335

Phe Ala Val Met Ser Gly Ser Ala Ala Leu Gly Thr Cys Leu Pro His
            340                 345                 350

Leu Asn Thr Ile Ser Ile Ala Arg Gly Ala Val Arg Ser Val Leu Ser
        355                 360                 365

Val Ile Asn Ser Arg Pro Lys Ile Asp Pro Tyr Ser Leu Asp Gly Ile
    370                 375                 380

Val Leu Asn Asn Met Arg Gly Ser Ile Arg Phe Lys Asn Val His Phe
385                 390                 395                 400

Ser Tyr Pro Ser Arg Arg Thr Leu Gln Ile Leu Lys Gly Val Ser Leu
                405                 410                 415

Gln Val Ser Ala Gly Gln Lys Ile Ala Leu Val Gly Ser Ser Gly Cys
            420                 425                 430

Gly Lys Ser Thr Asn Val Asn Leu Leu Leu Arg Phe Tyr Asp Pro Thr
        435                 440                 445

Arg Gly Lys Val Thr Ile Asp Asp Ile Asp Val Cys Asp Leu Asn Val
    450                 455                 460

Gln Lys Leu Arg Glu Gln Ile Gly Val Val Ser Gln Glu Pro Val Leu
465                 470                 475                 480

Phe Asp Gly Thr Leu Phe Glu Asn Ile Lys Met Gly Tyr Glu Gln Ala
                485                 490                 495

Thr Met Glu Glu Val Gln Glu Ala Cys Arg Val Ala Asn Ala Ala Asp
            500                 505                 510

Phe Thr Lys Arg Leu Pro Glu Gly Tyr Gly Thr Arg Val Gly Glu Arg
        515                 520                 525

Gly Val Gln Leu Ser Gly Gly Lys Gln Arg Ile Ala Ile Ala Arg
    530                 535                 540

Ala Ile Ile Lys Asn Pro Arg Ile Leu Leu Leu Asp Glu Ala Thr Ser
545                 550                 555                 560

Ala Leu Asp Thr Glu Ala Glu Ser Ile Val Gln Glu Ala Leu Glu Lys
                565                 570                 575

Ala Gln Lys Gly Arg Thr Thr Val Ile Val Ala His Leu Arg Ser Thr
            580                 585                 590

Ile Arg Asn Val Asp Gln Ile Phe Val Phe Lys Asn Gly Thr Ile Val
        595                 600                 605

Glu Gln Gly Thr His Ala Glu Leu Met Asn Lys Arg Gly Val Phe Phe
    610                 615                 620

Glu Met Thr Gln Ala Gln Val Leu Arg Gln Glu Lys Glu Glu Glu Val
```

-continued

```
            625                 630                 635                 640
Leu Asp Ser Asp Ala Glu Ser Asp Val Val Ser Pro Asp Ile Ala Leu
                645                 650                 655

Pro His Leu Ser Ser Leu Arg Ser Arg Lys Glu Ser Thr Arg Ser Ala
                660                 665                 670

Ile Ser Ala Val Pro Ser Val Arg Ser Met Gln Ile Glu Met Glu Asp
                675                 680                 685

Leu Arg Ala Lys Pro Thr Pro Met Ser Lys Ile Phe Tyr Phe Asn Arg
                690                 695                 700

Asp Lys Trp Gly Tyr Phe Ile Leu Gly Leu Ile Ala Cys Ile Ile Thr
705                 710                 715                 720

Gly Thr Val Thr Pro Thr Phe Ala Val Leu Tyr Ala Gln Ile Ile Gln
                725                 730                 735

Val Tyr Ser Glu Pro Val Asp Gln Met Lys Gly His Val Leu Phe Trp
                740                 745                 750

Cys Gly Ala Phe Ile Val Ile Gly Leu Val His Ala Phe Ala Phe Phe
                755                 760                 765

Phe Ser Ala Ile Cys Leu Gly Arg Cys Gly Glu Ala Leu Thr Lys Lys
                770                 775                 780

Leu Arg Phe Glu Ala Phe Lys Asn Leu Leu Arg Gln Asn Val Gly Phe
785                 790                 795                 800

Tyr Asp Asp Ile Arg His Gly Thr Gly Lys Leu Cys Thr Arg Phe Ala
                805                 810                 815

Thr Asp Ala Pro Asn Val Arg Tyr Val Phe Thr Arg Leu Pro Gly Val
                820                 825                 830

Leu Ser Ser Val Val Thr Ile Ile Gly Ala Leu Val Ile Gly Phe Ile
                835                 840                 845

Phe Gly Trp Gln Leu Ala Leu Ile Leu Met Val Met Val Pro Leu Ile
                850                 855                 860

Ile Gly Ser Gly Tyr Phe Glu Met Arg Met Gln Phe Gly Lys Lys Met
865                 870                 875                 880

Arg Asp Thr Glu Leu Leu Glu Glu Ala Gly Lys Val Ala Ser Gln Ala
                885                 890                 895

Val Glu Asn Ile Arg Thr Val His Ala Leu Asn Arg Gln Glu Gln Phe
                900                 905                 910

His Phe Met Tyr Cys Glu Tyr Leu Lys Glu Pro Tyr Arg Glu Asn Leu
                915                 920                 925

Cys Gln Ala His Thr Tyr Gly Gly Val Phe Ala Phe Ser Gln Ser Leu
                930                 935                 940

Leu Phe Phe Met Tyr Ala Val Ala Phe Trp Ile Gly Ala Ile Phe Val
945                 950                 955                 960

Asp Asn His Ser Met Gln Pro Ile Asp Val Tyr Arg Val Phe Phe Ala
                965                 970                 975

Phe Met Phe Cys Gly Gln Met Val Gly Asn Ile Ser Ser Phe Ile Pro
                980                 985                 990

Asp Val Val Lys Ala Arg Leu Ala Ala Ser Leu Leu Phe Tyr Leu Ile
                995                 1000                1005

Glu His Pro Ser Glu Ile Asp Asn Leu Ser Glu Asp Gly Val Thr Lys
                1010                1015                1020

Lys Ile Ser Gly His Ile Ser Phe Arg Asn Val Tyr Phe Asn Tyr Pro
1025                1030                1035                1040

Thr Arg Arg Gln Ile Arg Val Leu Arg Gly Leu Asn Leu Glu Ile Asn
                1045                1050                1055
```

Pro Gly Thr Thr Val Ala Leu Val Gly Gln Ser Gly Cys Gly Lys Ser
        1060                1065                1070

Thr Val Met Ala Leu Leu Glu Arg Phe Tyr Asn Gln Asn Lys Gly Val
    1075                1080                1085

Ile Thr Val Asp Gly Glu Asn Ile Arg Asn Met Asn Ile Arg Asn Leu
        1090                1095                1100

Arg Glu Gln Val Cys Ile Val Ser Gln Glu Pro Thr Leu Phe Asp Cys
1105                1110                1115                1120

Thr Ile Met Glu Asn Ile Cys Tyr Gly Leu Asp Asp Pro Lys Pro Ser
            1125                1130                1135

Tyr Glu Gln Val Val Ala Ala Ala Lys Met Ala Asn Ile His Asn Phe
        1140                1145                1150

Val Leu Gly Leu Pro Glu Gly Tyr Asp Thr Arg Val Gly Glu Lys Gly
        1155                1160                1165

Thr Gln Leu Ser Gly Gly Gln Lys Gln Arg Ile Ala Ile Ala Arg Ala
    1170                1175                1180

Leu Ile Arg Asp Pro Pro Ile Leu Leu Leu Asp Glu Ala Thr Ser Ala
1185                1190                1195                1200

Leu Asp Thr Glu Ser Glu Lys Ile Val Gln Asp Ala Leu Glu Val Ala
            1205                1210                1215

Arg Gln Gly Arg Thr Cys Leu Val Ile Ala His Arg Leu Ser Thr Ile
        1220                1225                1230

Gln Asp Ser Asp Val Ile Val Met Ile Gln Glu Gly Lys Ala Thr Asp
        1235                1240                1245

Arg Gly Thr His Glu His Leu Leu Met Lys Asn Asp Leu Tyr Lys Arg
    1250                1255                1260

Leu Cys Glu Thr Gln Arg Leu Val Glu Ser Gln
1265                1270                1275

(2) INFORMATION FOR SEQ ID NO: 7:

(i) SEQUENCE CHARACTERISTICS:
        (A) LENGTH: 3512 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 7:

CCCGTTGTTG CCGGTGCTAT AGCGGAGGAG ACTTTCTCAT CGATACGAAC CGTACACTCG      60

TTATGTGGCC ATAAAAGAGA GCTAACAAGG CAGCGTTGGA GAAAGGACGT CAGACAGGCC     120

TTGTCAAATA TTTCTATATG GGTGTTGGTG TGAGATTTGG TCAGATGTGT ACCTATGTGT     180

CCTACGCCTT GGCTTTTTGG TATGGCAGTG TACTGATCAT CAACGACCCT GCATTGGATC     240

GTGGCCGAAT TTTCACAGTC TTTTTGCTGT GATGTCCGGC TCAGCAGCTC TCGGCACATG     300

TCTGCCACAT CTTAACACCA TATCCATCGC TCGAGGAGCG GTACGAAGTG TACTGTCAGT     360

GATTAATAGT CGTCCAAAAA TCGATCCCTA TTCGTTAGAT GGCATTGTGC TCAACAATAT     420

GAGAGGATCT ATTCGCTTCA GAACGTGCA TTTCTCCTAT CCTTCCCGAA GAACATTGCA      480

GATATTGAAA GGTGTGTCAC TGCAAGTGTC GGCTGGCCAA AAAATTGCTT TGGTGGGTTC     540

AAGCGGTTGT GGAAAGTCAA CGATCGTCAA TTTATTATTG AGATTTTATG ATCCGACAAG     600

GGGAAAGGTA ACCATAGATG ATATTGATGT GTGTGATCTC AACGTGCAAA ACTTCGTGA      660

ACAAATCGGT GTTGTTAGTC AGGAACCAGT GCTTTTCGAT GGCACACTAT TCGAAAATAT     720

```
CAAGATGGGT TATGAACAGG CCACAATGGA GGAGGTCCAA GAAGCGTGCC GTGTGGCGAA    780

TGCTGCCGAC TTCATCAAAC GACTTCCAGA AGGTTACGGC ACCCGAGTTG GTGAACGTGG    840

TGTGCAGTTA AGTGGCGGAC AAAAGCAGCG AATTGCCATA GCTCGTGCGA TCATCAAGAA    900

CCCTCGCATA CTGCTGCTCG ATGAAGCCAC CAGTGCTCTA GACACAGAAG CGGAATCAAT    960

CGTGCAAGAG GCTCTGGAGA AGGCTCAAAA AGGGAGAACA ACCGTCATTG TAGCGCATCG   1020

TCTGTCTACT ATCAGAAACG TGGATCAGAT TTTCGTTTTC AAGAACGGAA CGATCGTTGA   1080

GCAGGGCACT CATGCCGAGT TGATGAACAA ACGTGGAGTA TTCTTTGAAA TGACTCAAGC   1140

ACAAGTCCTC CGACAAGAGA AGGAAGAGGA AGTTTTAGAA AATACGGAAC CAGTAGCGAA   1200

GTGTCAAGAG GTATCCCTCC CTGCTCCTGA TGTCACTATT TTGGCTCCCC ATGAGGAACA   1260

ACCCGAGCTA CCTAGCCCGC CGGGTCGGTT AGAAAATACA AAGCAACATG AGCATCTCTG   1320

AATGTCTTTG TCTGAGATAG CGATGCGAAA TCCGATGTCG TGTCACCGGA TATTGCATTA   1380

CCCCATCTTA GTTCACTTCG ATCCCGTAAA GAATCCACAA GAAGTGCTAT CTCCGCGGTC   1440

CCCAGCGTTC GAAGTATGCA AATCGAAATG GAGGACCTTC GTGCCAAACC AACTCCAATG   1500

TCGAAAATTT CTATTTTAA CCGTGACAAA TGGGCATATT TCATTTTGGG ACTCATCGCC   1560

TGTATTATTA CTGGAACTGT TACACCGACA TTTGCAGTTT TATATGCGCA GATCATACAG   1620

GTATACTCGG AACCTGTTGA TCAAATGAAA GGCCATGTGC TGTTCTGGTG TGGAGCTTTC   1680

ATCGTCATTG GTCTCGTACA CGCTTTTGCG TTCTTTTTCT CGGCTATTTG TTTGGGACGT   1740

TGCGGCGAAG CGTTAACGAA AAAATTACGT TTCGAGGCGT TCAAGAACCT TCTGCGACAG   1800

GATGTGGGAT TCTACGACGA TATCCGACAC GGTACCGGTA AACTCTGTAC GCGATTTGCT   1860

ACAGATGCAC CCAATGTCCG ATATGTGTTC ACTCGACTTC CGGGTGTGCT TTCATCGGTG   1920

GTGACCATAA TTGGAGCTTT GGTTATTGGA TTCATCTTCG GGTGGCAGCT GGCTTTGATT   1980

CTTATGGTGA TGGTACCGTT GATCATCGGT AGTGGATACT TCGAGATGCG CATGCAGTTT   2040

GGTAAGGAGA TGCGTGACAC AGAGCTTCTT GAAGAGGCTG GGAAAGTTGC CTCTCAAGCC   2100

GTGGAGAACA TTCGTACCGT GCATGCCCTG AATAGGCAAG AGCAGTTCCA TTTCATGTAT   2160

TGCGAGTATT TGAAGGAACC CTATCGAGAA AATCTTTGCC AGGCGCACAC CTACGGGGGT   2220

GTATTCGCGT TCTCACAATC GTTGTTATTC TTTATGTATG CTGTAGCATT TTGGATTGGT   2280

GCAATCTTCG TGGACAACCA CAGCATGCAA CCGATTGACG TTTACCGAGT ATTTTTCGCG   2340

TTCATGTTTT GTGGACAAAT GGTCGGCAAC ATTTCTTCTT TTATTCCTGA CGTTGTGAAA   2400

GCTCGCCTGG CTGCATCGCT CCTTTTCTAC CTTATCGAAC ACCCATCAGA AATTGATAAT   2460

TTGTCCGAGG ATGGTGTCAC GAAGAAAATC TCTGGTCATA TCTCGTTCCG CAATGTCTAT   2520

TTCAATTATC CGACAAGAAG ACAGATCAGA GTACTCCGTG GACTTAACCT AGAGATAAAT   2580

CCTGGCACGA AGGTAGCGCT TGTTGGGCAG TCTGGTTGTG GAAAAAGCAC TGTGATGGCG   2640

TTGTTGGAAC GGTTTTACAA TCAAAACAAG GGCGTGATTA CGGTGGACGG CGAAAACATC   2700

AGAAACATGA ACATACGCAA TCTTCGTGAG CAAGTGTGTA TTGTAAGCCA GGAACCAACG   2760

CTGTTCGACT GTACCATCAT GGAAAACATC TGTTACGGTC TCGATGACCC CAAGCCGTCC   2820

TACGAACAGG TTGTTGCTGC AGCAAAAATG GCGAACATTC ACAATTTTGT GCTGGGACTA   2880

CCAGAGGGTT ACGATACGCG TGTTGGTGAG AAAGGCACTC AGCTGTCAGG CGGACAGAAG   2940

CAACGAATAG CCATAGCCAG AGCGCTGATT CGAGATCCGC CTATACTTCT GCTGGATGAG   3000

GCGACAAGCG CGCTGGATAC CGAGAGTGAA AAGATCGTGC AAGACGCCCT AGAGGTTGCT   3060
```

| CGCCAAGGTA | GAACGTGCCT | TGTAATTGCC | CATCGCCTTT | CTACAATTCA | AGACAGTGAC | 3120 |
| GTCATAGTGA | TGATCCAGGA | GGGGAAAGCT | ACAGACAGAG | GCACTCATGA | ACATTTACTG | 3180 |
| ATGAAGAACG | ATCTATACAA | ACGGCTATGC | GAAACACAAC | GACTCGTTGA | ATCACAATGA | 3240 |
| GTTTTTAGTG | CCAATCGATA | GTGATCGATA | AGCTATGGAT | TAGTCTTTAA | CACTTACTGA | 3300 |
| TCACAAATTT | TATCTCGTGC | TTTATTCTAA | TGTACATATG | TAACGGTTTT | GATCTTACAT | 3360 |
| ATCTTGTAAT | TGGTCCTCAC | TATCATAATG | CCTTTAGTAG | TACATTAACA | GTTTTATTAA | 3420 |
| TACAACTTAA | GTAACATATT | AACAATTTTA | TTAATATAAC | TTAAGTAAGA | TATTGACAGT | 3480 |
| TTTATTAATT | TGGAGGATTT | ATAATAAAAC | TT | | | 3512 |

(2) INFORMATION FOR SEQ ID NO: 8:

(i) SEQUENCE CHARACTERISTICS:
        (A) LENGTH: 2681 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 8:

| CCCGACTTCC | GGAAGGTTAC | GGCACCCGAG | TAGGTGAACG | TGGTGTACAA | CTAAGTGGCG | 60 |
| GACAAAAGCA | GCGCATCGCT | ATTGCTCGCG | CCATCATTAA | AAACCCTCGT | ATACTTCTGC | 120 |
| TTGACGAAGC | CACCAGTGCT | CTGGACACAG | AGGCGGAATC | AATTGTGCAA | GAAGCTCTCG | 180 |
| AGAAAGCTCA | AAAGGACGA | ACGACCGTCA | TTGTAGCGCA | TCGCCTATCT | ACCATCAGAA | 240 |
| ATGTCGATCA | AATTTTCGTC | TTCAAGAATG | AAACGATTGT | TGAGCAGGGT | ACACATGCAG | 300 |
| AGTTGATGAA | CAAACGAGGA | GTGTTCTTTG | AAATGACTCA | AGCACAGGTC | CTTCGACAAG | 360 |
| AAAAGGAAGA | GGAGGTCTTA | GAAAATACGG | AACCAGTAGC | GAAGTGTCAA | GAGGCATCCT | 420 |
| TTCCTGCTCC | TGATGTCACT | ATTTTGACTC | CCCATGACGA | ACAACCCGAG | CTACTTAGCC | 480 |
| CGCCGGATAG | CGATGCGGAA | TCCGACGTCA | TGTCACCGGA | TCTTGGCTTA | CCCCATCTTA | 540 |
| GTTCACTTCG | ATCACGTAAA | GAGTCCACAA | GAAGTGCTAT | TTCCGCAGTC | CCAGCGTTC | 600 |
| GGAGTATGCA | GATCGAAATG | GAGGACCTTC | GTGCCAAACC | GACTCCGATG | TCGAAAATTT | 660 |
| TCTATTTCAA | CCGTGACAAA | TGGGGATTTT | TCATTTTGGG | ACTCATCGCC | TGTATTATAA | 720 |
| CTGGAACTGT | TACACCGACA | TTTGCAGTTT | TATATGCGCA | GATCATACAG | GTATACTCGG | 780 |
| AACCTGTTGA | TCAAATGAAA | GGCCATGTGC | TGTTTTGGTG | TGGAGCTTTC | ATCGTCATTG | 840 |
| GTCTCGTACA | CGCATTTGCG | TTCTTTTTCT | CGGCCATTTG | TCTGGGACGT | TGCGGCGAAG | 900 |
| CTTTAACGAA | GAAGTTACGT | TTCGAGGCGT | TCAAGAACCT | TCTCCGACAA | GATGTGGGAT | 960 |
| TCTACGACGA | TATCCGACAC | GGTACCGGTA | AACTCTGTAC | GCGATTTGCT | ACAGATGCAC | 1020 |
| CCAATGTTCG | ATATGTGTTC | ACTCGACTTC | CGGGTGTACT | TCATCGGTG | GTGACCATAA | 1080 |
| TCGGAGCTTT | GGTTATTGGA | TTTATTTTCG | GGTGGCAGCT | GGCCTTGATT | CTTATGGTCA | 1140 |
| TGGTACCGTT | GATCATTGGC | AGTGGATACT | TCGAGATGCG | CATGCAGTTT | GGTAAAAAGA | 1200 |
| TGCGTGACAC | AGAGCTTCTT | GAAGAGGCTG | GGAAAGTTGC | CTCACAAGCC | GTAGAGAATA | 1260 |
| TTCGTACCGT | ACATGCCCTG | AATCGGCAAG | AGCAGTTCCA | TTTCATGTAC | TGCGAGTATT | 1320 |
| TGAAGGAACC | CTATCGAGAG | AATCTTTGCC | AGGCGCACAC | TTACGGGGGT | GTATTCGCGT | 1380 |
| TTTCACAGTC | GTTGTTATTC | TTTATGTATG | CTGTAGCATT | TTGGATTGGT | GCAATCTTCG | 1440 |
| TGGACAACCA | CAGCATGCAA | CCGATTGATG | TTTACCGAGT | ATTTTTCGCG | TTCATGTTTT | 1500 |

-continued

```
GTGGACAAAT GGTTGGCAAC ATTTCGTCCT TCATCCCTGA TGTTGTGAAA GCTCGCCTGG    1560

CTGCATCGCT CCTTTTCTAC CTCATCGAAC ACCCATCAGA AATTGATAAC TTGTCCGAGG    1620

ATGGTGTCAA GAAGAAAATC TCTGGTCACA TCTCGTTCCG CAATGTCTAT TTCAATTACC    1680

CGACGAGAAG GCAGATCAGA GTACTCCGTG GACTTAACCT AGAGATAAAT CCTGGCACGA    1740

CGGTAGCGCT TGTTGGACAA TCTGGTTGTG GAAAAAGCAC TGTGATGGCG TTGTTGGAAC    1800

GCTTTTACAA TCAAAACAAG GGCGTGATTA CGGTTGACGG CGAAAACATC AGAAACATGA    1860

ACATACGCAA TCTCCGTGAG CAAGTATGTA TAGTCAGCCA GGAACCAACA CTGTTCGACT    1920

GTACCATCAT GGAAACATC TGTTACGGAC TCGATGACCC CAAACCGTCC TACGAACAGG     1980

TTGTTGCGGC AGCAAAAATG GCGAACATCC ACAATTTTGT GCTGGGACTG CCAGAGGGTT    2040

ATGACACGCG TGTTGGCGAG AAAGGCACTC AGCTGTCAGG CGGACAAAAG CAAGAATAG     2100

CCATAGCCCG AGCGCTGATC CGAGATCCGC CTATACTTCT GCTGGATGAG GCGACAAGCG    2160

CTCTGGACAC GGAGAGTGAG AAGATCGTGC AAGACGCCCT AGAGGTTGCT CGCCAAGGTA    2220

GAACGTGCCT TGTAATTGCC CACCGCCTTT CTACAATTCA AGACAGTGAC GTCATAGTGA    2280

TGATCCAGGA GGGAAAAGCT ACAGACAGAG GCACTCATGA ACATTTACTG ATGAAGAACG    2340

ATCTATACAA ACGGCTATGC GAAACACAAC GACTCGTTGA ATCACAATGA GTTTTTAGTG    2400

CCGATCGATA GTGATCGATA AGCTATGGAT TAGTCTTCAA CACTTACTGA TCATATGACT    2460

ATCTCGTGCT TTATTATAAT GTACATATGT AATGGTTTTG ATGTAAGTTA AGTTATAATT    2520

GGTCTTCACT ATCATAATGC CTTTAGTAAT GCATTAACAC TTTTATAATA TAACTTGAAT    2580

AACATATTGA CAGTTTTATT AATATAACTT AAATAAGATA TTGACAGTTT TATTAATTTG    2640

GAGAATTTAT AATGAAACTT CTGGATTCCT GCAGCCCGGG G                       2681
```

(2) INFORMATION FOR SEQ ID NO: 9:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
GAAATGACTC AAGCACAAG                                                  19
```

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 10:

```
AGACAAAGAC ATTCAGAG                                                   18
```

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear

```
        (ii) MOLECULE TYPE: cDNA (xi) SEQUENCE DESCRIPTION: SEQ ID NO: 11:

ACNGTNGCNY TNGTNGG                                                        17

(2) INFORMATION FOR SEQ ID NO: 12:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 12:

GCNSWNGTNG CYTCRTC                                                        17
```